(12) United States Patent
Sohn et al.

(10) Patent No.: US 9,719,991 B2
(45) Date of Patent: Aug. 1, 2017

(54) DEVICES FOR DETECTING A PARTICLE IN A SAMPLE AND METHODS FOR USE THEREOF

(71) Applicant: The Regents of the University of California, Oakland, CA (US)

(72) Inventors: Lydia Lee Sohn, Oakland, CA (US); Karthik Balakrishnan, Berkeley, CA (US); George Anwar, El Sobrante, CA (US); Matthew Rowe Chapman, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/843,861

(22) Filed: Sep. 2, 2015

(65) Prior Publication Data
US 2016/0061826 A1    Mar. 3, 2016

Related U.S. Application Data

(63) Continuation of application No. 14/239,987, filed as application No. PCT/US2012/059088 on Oct. 5, 2012, now Pat. No. 9,201,043.
(Continued)

(51) Int. Cl.
*G01N 33/543*    (2006.01)
*G01N 33/50*    (2006.01)
(Continued)

(52) U.S. Cl.
CPC .... *G01N 33/5438* (2013.01); *B01L 3/502761* (2013.01); *G01N 15/1056* (2013.01);
(Continued)

(58) Field of Classification Search
CPC ............. G01N 21/05; G01N 27/44791; G01N 33/5438; G01N 2015/149; G01N 27/30;
(Continued)

(56) References Cited

U.S. PATENT DOCUMENTS 4,778,657 A    10/1988  Spohr
7,279,883 B2   10/2007  Sohn et al.
(Continued)

FOREIGN PATENT DOCUMENTS

EP    0187663    7/1986
EP    2311975    4/2011
(Continued)

OTHER PUBLICATIONS

Carbonaro et al, "Cell characterization using a protein-functionalized pore" Lab Chip, 2008, 8, pp. 1478-1485.*
(Continued)

*Primary Examiner* — Dennis M White
(74) *Attorney, Agent, or Firm* — Rudy J. Ng; Bret E. Field; Bozicevic, Field & Francis LLP

(57) ABSTRACT

Devices for detecting a particle in a fluid sample are provided. The device includes a segmented microfluidic conduit configured to carry a flow of a fluid sample, where the conduit includes one or more nodes and two or more sections, and a node is positioned between adjacent sections of the conduit. The device also includes a detector configured to detect a change in current through the conduit. Also provided are methods of using the devices as well as systems and kits that include the devices. The devices, systems and methods find use in a variety of different applications, including diagnostic assays.

21 Claims, 16 Drawing Sheets

Related U.S. Application Data

(60) Provisional application No. 61/544,232, filed on Oct. 6, 2011.

(51) Int. Cl.

| | | |
|---|---|---|
| *G01N 27/447* | (2006.01) | |
| *G01N 33/487* | (2006.01) | |
| *G01N 27/327* | (2006.01) | |
| *G01N 27/403* | (2006.01) | |
| *G01N 27/49* | (2006.01) | |
| G01N 15/14 | (2006.01) | |
| B01L 9/00 | (2006.01) | |
| G01N 27/30 | (2006.01) | |
| G01N 21/05 | (2006.01) | |
| B01L 3/00 | (2006.01) | |
| G01N 15/10 | (2006.01) | |

(52) U.S. Cl.
CPC ....... *G01N 27/3275* (2013.01); *G01N 27/403* (2013.01); *G01N 27/44791* (2013.01); *G01N 27/49* (2013.01); *G01N 33/48721* (2013.01); *G01N 33/5005* (2013.01); *G01N 33/54313* (2013.01); *B01L 3/502715* (2013.01); *B01L 9/527* (2013.01); *B01L 2200/0652* (2013.01); *B01L 2200/0668* (2013.01); *B01L 2200/16* (2013.01); *B01L 2300/0636* (2013.01); *B01L 2300/0645* (2013.01); *B01L 2300/087* (2013.01); *B01L 2300/0816* (2013.01); *B01L 2300/0819* (2013.01); *B01L 2300/0838* (2013.01); *B01L 2300/0867* (2013.01); *B01L 2400/084* (2013.01); *G01N 21/05* (2013.01); *G01N 27/30* (2013.01); *G01N 2015/1006* (2013.01); *G01N 2015/149* (2013.01)

(58) Field of Classification Search
CPC ........... G01N 15/1056; G01N 27/3275; G01N 27/49; G01N 27/403; G01N 33/48721; G01N 33/5005; G01N 33/54313; G01N 2015/1006; B01L 3/502715; B01L 2300/0636; B01L 2300/0816; B01L 2200/16; B01L 2200/0668; B01L 2300/0867; B01L 2300/087; B01L 2200/0652; B01L 2300/0819; B01L 2300/0838; B01L 9/527; B01L 2300/0645; B01L 3/502761
See application file for complete search history.

(56) References Cited

U.S. PATENT DOCUMENTS

| | | |
|---|---|---|
| 2008/0093229 A1 | 4/2008 | Lim et al. |
| 2008/0317632 A1* | 12/2008 | Shimasaki ......... B01D 19/0031 422/68.1 |
| 2010/0099198 A1 | 4/2010 | Zhao et al. |
| 2010/0221769 A1 | 9/2010 | Lu et al. |

FOREIGN PATENT DOCUMENTS

| | | |
|---|---|---|
| KR | 10-0830221 | 5/2008 |
| WO | 2005095935 | 10/2005 |
| WO | 2010007537 | 1/2010 |

OTHER PUBLICATIONS

Carbonaro et al. (2008) "Cell characterization using a protein-functionalized pore," Lab on a Chip;8(9):1478-1485.

Chapman and Sohn (2011) "Chapter 6: Label-Free Resistive-Pulse Cytometry," Methods in Cell Biology; 102:127-157.

* cited by examiner

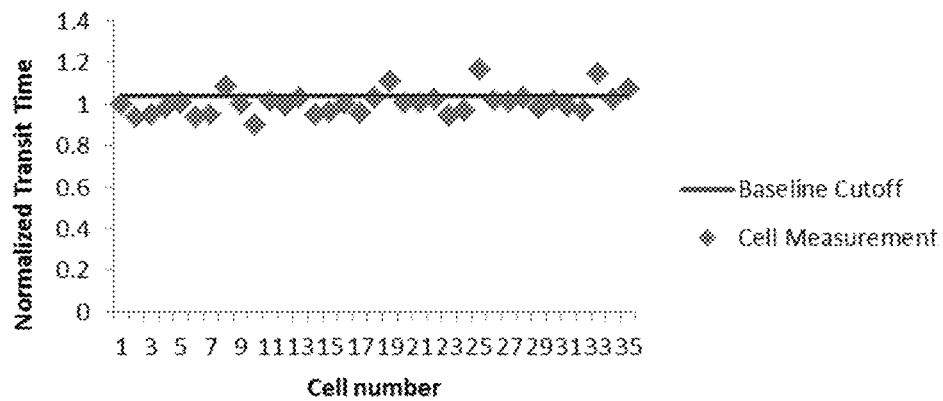
(c)
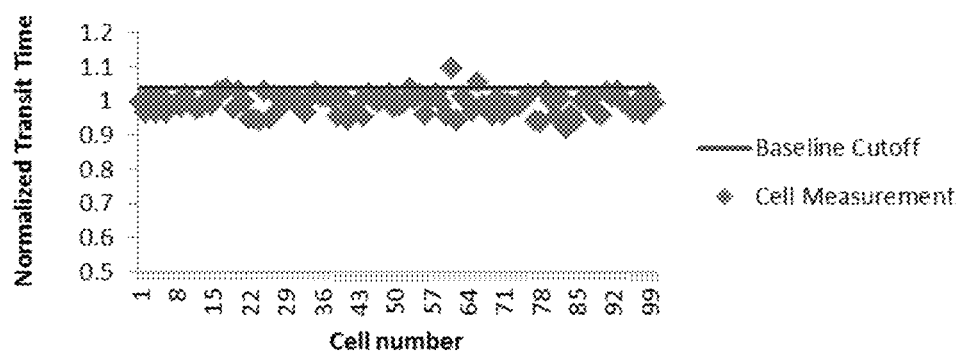
(d)
FIG. 13, continued (a)

(b)

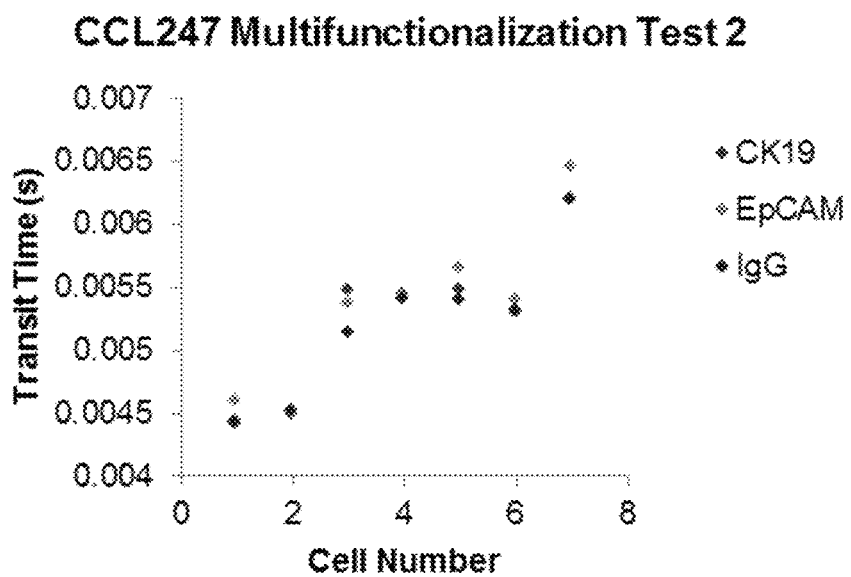
(c)
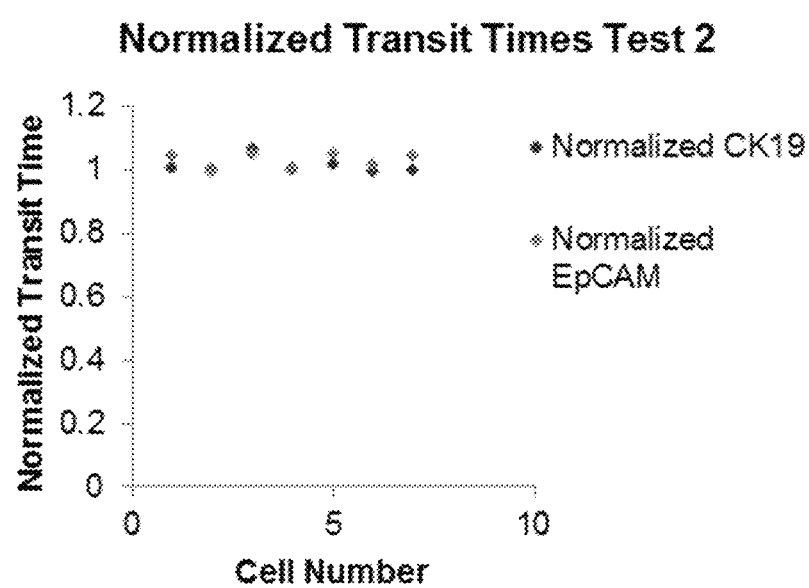
(d)
FIG. 14, continued

DEVICES FOR DETECTING A PARTICLE IN A SAMPLE AND METHODS FOR USE THEREOF

CROSS-REFERENCE TO RELATED APPLICATIONS

This patent application is a continuation of U.S. application Ser. No. 14/239,987, filed Feb. 20, 2014, which is a National Stage entry of International Application No. PCT/US2012/059088, filed Oct. 5, 2012, which claims the benefit of priority under 35 U.S.C. §119(e) to U.S. Provisional Patent Application Nos. 61/544,232, filed Oct. 6, 2011, the disclosure of which is hereby incorporated by reference in its entirety.

INTRODUCTION

Cell characterization through identification of membrane components is used in cell biology for disease diagnosis and monitoring, and drug discovery. Although current methods for cell analysis, such as flow cytometry and magnetic-bead column selection have been used in both research laboratories and clinical settings, improved devices and methods may be desirable. For example, traditional approaches often require advanced preparation, including exogenous labeling of cells. Such labeling leads to added incubation time, additional costs, loss of sample, and the possibility of modifying cell physiology and function. As another example, data analysis can be challenging when the available number of cells to be screened is on the order of just a few hundred or less. Finally, traditional approaches do not lend themselves to portability, which can be desirable in certain clinical situations.

SUMMARY

Devices for detecting a particle in a fluid sample are provided. The device includes a segmented microfluidic conduit configured to carry a flow of a fluid sample, wherein the conduit comprises one or more nodes and two or more sections, and a node is positioned between adjacent sections of the conduit. The device also includes a detector configured to detect a change in current through the conduit. Also provided are methods of using the devices as well as systems and kits that include the devices. The devices, systems and methods find use in a variety of different applications, including diagnostic assays.

Embodiments of the present disclosure include a device for detecting a particle in a fluid sample. The device includes a segmented microfluidic conduit configured to carry a flow of a fluid sample, where the conduit includes one or more nodes and two or more sections, and a node is positioned between adjacent sections of the conduit. The device also includes a detector configured to detect a change in current through the conduit.

In some embodiments, the node has a diameter greater than the diameter of the conduit.

In some embodiments, the detector is configured to apply a current or a voltage through the conduit to produce a signal that corresponds to the presence of the particle in the conduit. In some embodiments, the current is AC.

In some embodiments, the one or more of the sections includes a functionalized surface. In some embodiments, the functionalized surface includes a binding member, such as an antibody, a protein, a sugar molecule or an aptamer. In some embodiments, the binding member is configured to specifically interact with a biomarker on the particle. In some embodiments, two or more of the sections include functionalized surfaces, and the two or more sections include different functionalized surfaces.

In some embodiments, the conduit includes two or more nodes. In some embodiments, the nodes are equally spaced along the conduit. In some embodiments, the nodes are unequally spaced along the conduit.

Embodiments of the present disclosure include a method of detecting a particle in a fluid sample. The method includes passing a fluid sample that includes a particle through a segmented microfluidic conduit, where the conduit includes one or more nodes and two or more sections, where a node is positioned between adjacent sections of the conduit. The method also includes applying a current or a voltage through the conduit to produce a detectable signal that corresponds to the presence of the particle in the conduit.

In some embodiments, the method further includes detecting the signal to determine the presence of the particle in the conduit.

In some embodiments, the method further includes quantifying the particle that passes through the conduit. In some embodiments, the method further includes characterizing the particle as the particle passes through the conduit. In some embodiments, the characterizing includes determining whether a biomarker is present on the particle based on the signal.

In some embodiments, the particle is a cell, a virus, DNA or RNA.

Embodiments of the present disclosure include a system for detecting a particle in a fluid sample. The system includes a device that includes a segmented microfluidic conduit configured to carry a flow of a fluid sample, and a fluid handling system configured to provide the flow of the fluid sample through the conduit. The conduit includes one or more nodes and two or more sections, and a node is positioned between adjacent sections of the conduit. The device also includes a detector configured to detect a change in current through the conduit.

In some embodiments, the system further includes a sorter positioned downstream from the device.

Embodiments of the present disclosure include a kit that includes a device and a buffer. The device includes a segmented microfluidic conduit configured to carry a flow of a fluid sample, where the conduit includes one or more nodes and two or more sections, and a node is positioned between adjacent sections of the conduit. The device also includes a detector configured to detect a change in current through the conduit.

BRIEF DESCRIPTION OF THE FIGURES

FIG. 1(panel b) shows the corresponding transient three-pulse current reading as a particle passes through the three sections of the conduit, according to embodiments of the present disclosure.

FIG. 3A(panel (i)) shows a fluorescent image of a conduit with no nodes (left) with the current pulse generated (right). FIG. 3A(panel (ii)) shows a fluorescent image of a conduit segmented into three sections of equal length using two nodes (left) with the corresponding current measurement (right). Two current spikes were detected in the signal due to the presence of the two nodes. FIG. 3A(panel (iii)) shows a fluorescent image of a node-conduit segmented into twelve regions using eleven equally spaced nodes (left) and the signal generated (right) with eleven current spikes of equal spacing. FIG. 3A(panel (iv)) shows a fluorescent image of a conduit segmented into eight sections of varying size using seven variably spaced nodes (left) and the signal generated (right). The variably spaced current spikes corresponded to the variably spaced nodes. AG. 3B shows a schematic of a particle in a conduit, according to embodiments of the present disclosure. AG. 3B(panel (i)) shows a schematic showing a spherical non-conducting particle of radius $r_{particle}$ in a conduit of radius $r_{conduit}$ and filled with conducting fluid of resistivity $\rho_{fluid}$. The pore axis centered at the particle is shown as x, and a single cross-sectional slice is highlighted in grey. FIG. 3B(panel (iii)) shows a cross-sectional slice of a particle, in darker shading, within a rectangular pore of height H and width W. FIG. 3B(panel (iv)) shows a cross-sectional slice of a particle, in darker shading, within a rectangular node region of height H and width $W_{node} > W$.

FIG. 4(panel a) shows a fluorescent image of a conduit containing four nodes. FIG. 4(panel b) shows a current measurement of a 5 µm colloid through the conduit. Four spikes within the pulse of the signal corresponded to increases in current as the colloid traveled through the nodes. FIG. 4(panel c) shows the signal detected for a 930 nm colloid transiting the same conduit. FIG. 4(panel d) shows the detection of a 500 nm colloid in the four-node conduit. FIG. 4(panel e) shows the detection of a 50 nm colloid transiting the same conduit, corresponding to a particle-to-conduit volume ratio of $1.2 \times 10^{-9}$.

FIG. 5(panel a) shows an image of a 18 µm×20 µm×2400 µm (H×W×L) long microfluidic device with two segmentation regions with different node spacing corresponding to 100 µm and 500 µm spacing in between two nodes of width 50 FIG. 5(panel b) shows the current signal generated as a 15.45 µm colloid traveled through the device. FIG. 5(panel c) shows the fast Fourier transform frequency spectrum of the total signal after ten total duplications of the data.

FIG. 6(panel a) shows an image of raw data during data acquisition. FIG. 6(panel b) shows an image of data after normalization to a baseline fit. FIG. 6(panel c) shows data after a low pass filter was applied. FIG. 6(panel d) shows data after regions of interest were identified and trimmed using derivative cutoff detection. FIG. 6(panel e) shows duplication of the trimmed data prior to FFT analysis. FIG. 6(panel f) shows calculation of the FFT of the duplication data.

FIG. 7(panel a) shows a graph of raw signal measurement of a sample of human plasma spiked with HIV at 100,000 copies/mL. After applying a low pass filter, the identification of the nanoscale HIV particles (magnified inset) was made and distinguished from larger particles present such as the highlighted 1 µm sized particles on the right. FIG. 7(panel b) shows measurement of particles in human plasma after processing 50 nL through the device. FIGS. 7(panel c)-7(panel e) shows measurement distribution of three samples of the same volume that were spiked with HIV. The distribution below 200 nm was indicative of HIV detection as this size distribution was not present when measuring the negative control sample.

DETAILED DESCRIPTION

Figure 1:
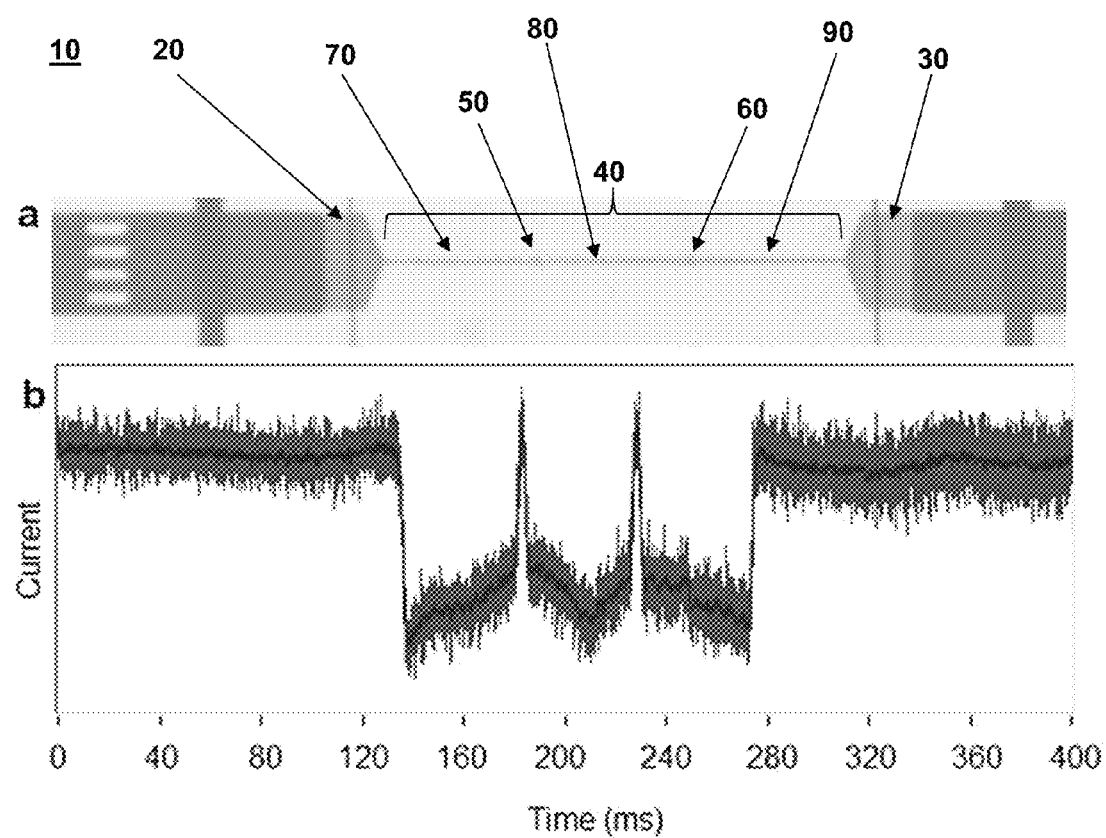
FIG. 1 (panel a) shows an image of a device that includes a conduit with two nodes and electrodes to perform a resistive-pulse reading, according to embodiments of the present disclosure.

Devices for detecting a particle in a fluid sample are provided. The device includes a segmented microfluidic conduit configured to carry a flow of a fluid sample, wherein the conduit comprises one or more nodes and two or more sections, and a node is positioned between adjacent sections of the conduit. The device also includes a detector configured to detect a change in current through the conduit. Also provided are methods of using the devices as well as systems and kits that include the devices. The devices, systems and methods find use in a variety of different applications, including diagnostic assays.

Before the present invention is described in greater detail, it is to be understood that aspects of the present disclosure are not limited to the particular embodiments described, and as such may, of course, vary. It is also to be understood that the terminology used herein is for the purpose of describing particular embodiments only, and is not intended to be limiting, since the scope of embodiments of the present disclosure will be defined only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within embodiments of the present disclosure. The upper and lower limits of these smaller ranges may independently be included in the smaller ranges and are also encompassed within embodiments of the present disclosure, subject to any specifically excluded limit in the stated range. Where the stated range includes one or both of the limits, ranges excluding either or both of those included limits are also included in embodiments of the present disclosure.

Unless defined otherwise, all technical and scientific terms used herein have the same meaning as commonly understood by one of ordinary skill in the art to which this invention belongs. Although any methods and materials similar or equivalent to those described herein can also be used in the practice or testing of embodiments of the present disclosure, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that embodiments of the present disclosure are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing various aspects of embodiments of the present disclosure, embodiments of the devices for detecting a particle in a fluid sample are described first in greater detail. Following this description, methods of detecting a particle in a fluid sample, followed by a description of embodiments of systems that include the devices are provided. Finally, a review of the various applications in which the devices, methods, and systems may find use is provided.

Devices

In certain embodiments, devices of the present disclosure are configured to detect changes in electrical current through a conduit as individual particles pass through the conduit. In some instances, particles in a sample solution flow through the conduit and in doing so, displace conducting fluid and raise the electrical resistance of the conduit. By monitoring the changes in electrical current through the conduit as individual particles pass through the conduit, the presence of the particle in the conduit may be detected, and, in some embodiments, the size of the particle and/or type of particle passing through the conduit may be determined.

In certain embodiments, devices of the present disclosure include a conduit configured to carry a flow of a fluid sample, and a detector configured to detect a change in current through the conduit. Each of these elements, as well as other aspects of the devices are described in more detail below.

Conduit

As described above, devices of the present disclosure include a conduit. The conduit is configured to carry a flow of a fluid sample. For example, the conduit may be in fluid communication at a first end with a first reservoir, and in fluid communication at a second end with a second reservoir. The conduit may be configured to carry a flow of a fluid from the first reservoir to the second reservoir.

In certain embodiments, the conduit has a diameter of 0.1 µm to 100 µm, such as 1 µm to 75 µm, including 10 µm to 50 µm. For example, the conduit may have a diameter of 25 µm. Although described in terms of diameter for circular cross sections, the dimensions described herein also apply to square or rectangular cross sectional conduits, such as the width and/or height of a square or rectangular cross section. In some cases, the conduit has a cross sectional area of 2500 $\mu m^2$ or less, or 2000 $\mu m^2$ or less, or 1500 $\mu m^2$ or less, or 1000 $\mu m^2$ or less, or 750 $\mu m^2$ or less, or 700 $\mu m^2$ or less, or 650 $\mu m^2$ or less, or 600 $\mu m^2$ or less, or 500 $\mu m^2$ or less. For instance, the conduit may have a cross sectional area of 650 $\mu m^2$ or less. The length of the conduit will generally be greater than its diameter. In some instances, the length of the conduit is 1 to 5000 µm, or 1 to 4500 µm, or 1 to 4000 µm, or 1 to 3500 µm, 1 to 3000 µm, 1 to 2500 µm, such as from 1 to 2000 µm, including from 10 to 1500 µm, or from 50 to 1000 µm, or from 50 to 750 µm. For example, the length of the conduit may be 2500 µm or less, such as 2000 µm or less, or 1500 µm or less, or 1000 µm or less, such as 900 µm or less, or 800 µm or less, or 700 µm or less, or 600 µm or less, or 500 µm or less. In certain instances, the ratio of the length of the conduit to the diameter will be 100:1, such as 75:1, including 50:1, or 40:1, or 30:1, or 25:1, or 20:1, or 15:1 or 10:1.

In certain embodiments, the volume of the conduit is 250 pL or more, or 500 pL or more, or 750 pL or more, or 1000 pL (i.e., 1 nL (nanoliter)) or more, or 1250 pL or more, or 1500 pL or more, or 1750 pL or more, or 2000 pL or more, or 2500 pL or more, or 3000 pL or more, or 3500 pL or more, or 4000 pL or more, or 4500 pL or more, or 5000 pL or more. In some instances, a larger conduit may be used, for example with a volume of 10 nL or more, or 50 nL or more, or 100 nL or more, or 250 nL or more, or 500 nL or more, or 750 nL or more, or 1000 nL or more, or 1500 nL or more, or 2000 nL or more, or 5000 nL or more, etc. In some cases, the volume ratio (e.g., the ratio of the volume of the particle to the volume of the conduit) will be from $1 \times 10^{-10}$ to 0.5; such as from $1 \times 10^{-9}$ to 0.2, including from $1 \times 10^{-8}$ to 0.1.

Although the dimensions of the conduit have been described above, the dimensions of conduit may vary as desired with the size and shape of the particles to be measured. The cross sectional profile of the conduit may be circular, square or rectangular. In certain embodiments, the cross sectional profile of the conduit is square. However, for some applications, it may be desired to use other conduit shapes. For example, for particles having a large aspect ratio, it may be desirable to use a rectangular conduit so that the particles may only transit through the conduit in a limited number of conformations.

In certain embodiments, the conduit includes one or more nodes positioned along the conduit. By "node" is meant a point or region along the conduit that has a diameter (or width for square or rectangular cross section) greater than the diameter of the conduit. In some cases, the node has a diameter that is 5% or more larger than the diameter of the conduit, such as 10% or more, including 25% or more, or 50% or more, or 100% or more, or 125% or more, or 150% or more, or 175% or more, or 200% or more, or 250% or more, or 300% or more, or 350% or more, or 400% or more, or 450% or more, or 500% or more larger than the diameter of the conduit. For instance, in certain embodiments, the node has a diameter of 1 μm to 100 μm, such as 5 μm to 75 μm, including 25 μm to 75 μm. For example, the node may have a diameter of 50 μm. In some cases, the node has a cross sectional area of 5000 μm$^2$ or less, such as 4000 μm$^2$ or less, including 3000 μm$^2$ or less, or 2500 μm$^2$ or less, or 2000 μm$^2$ or less, or 1500 μm$^2$ or less, or 1000 μm$^2$ or less, or 750 μm$^2$ or less. For instance, the node may have a cross sectional area of 2500 μm$^2$ or less. In certain embodiments, the node has a volume of 10 pL (picoliter) or more, such as 25 pL or more, or 50 pL or more, or 75 pL or more, or 100 pL or more, or 125 pL or more, or 150 pL or more, or 175 pL or more, or 200 pL or more.

The nodes may be positioned at any position(s) along the conduit between the ends of the conduit. In certain embodiments, the device includes a segmented (e.g., sectioned) conduit. By "segmented" or "sectioned" is meant that the conduit is divided into two or more sections. As such, the device includes a segmented microfluidic conduit configured to carry a flow of a fluid sample. The conduit includes one or more nodes and two or more sections. In some instances, a node is positioned between adjacent sections of the conduit. For example, each node may be flanked on each side by a section of the conduit. In some instances, an alternating pattern of conduit sections and nodes is present from the upstream end of the conduit to the downstream end of the conduit. For example, traversing the conduit from the upstream end to the downstream end, the conduit may have a first section, followed by a first node, followed by a second section, followed by a second node, followed by a third section, etc. As indicated above, the nodes may be positioned along the conduit such that a node is positioned between adjacent sections of the conduit. For example, in some embodiments, the conduit includes one node. In embodiments that include one node, the node may be positioned proximate to an end of the conduit, such as near the upstream end of the conduit, or may be positioned proximate to the downstream end of the conduit. By "upstream" is meant at a position nearer to the source of the fluid flow. By "downstream" is meant at a position further away from the source of the fluid flow. In other embodiments, the node may be positioned substantially in the middle of the conduit between the two ends of the conduit. Other embodiments of the conduit may include two or more nodes, such as 3 or more, including 4 or more, or 5 or more, or 6 or more, or 7 or more, or 8 or more, or 9 or more, or 10 or more, or 11 or more, or 12 or more, or 13 or more, or 14 or more, or 15 or more, or 20 or more, or 25 or more nodes. The nodes may be positioned along the conduit at regular intervals such that the distance between each node is substantially the same. In other cases, the nodes may be positioned along the conduit such that the distance between adjacent nodes is different.

In embodiments that include two or more nodes, each node may have the same shape and dimensions. In other embodiments, the nodes may have different shapes and/or dimensions. For example, a conduit may include two nodes, where the first node has the same diameter as the second node, but the first node has a length that is different from the second node. Other variations in the dimensions of the nodes are possible as desired.

A node may be positioned along the conduit such that the node is in fluid communication with the conduit. As such, a flow of a fluid sample through the conduit enters the conduit at a first end (e.g., the upstream end of the conduit), passes through the conduit and the one or more nodes positioned along the conduit, and then flows out a second end of the conduit (e.g., the downstream end of the conduit). In some cases, the node is aligned with an axis of the conduit, such as aligned with the longitudinal axis of the conduit. For instance, the node may have a central axis substantially aligned with the longitudinal axis of the conduit.

Because the node is positioned along the conduit, the node divides the conduit into different sections of the conduit. For n number of nodes, the conduit will be divided into n+1 number of sections. For example, in embodiments of the conduit that include one node, the node divides the conduit into two sections, such as a first section (e.g., an upstream section) and a second section (e.g., a downstream section). In embodiments that include two nodes, the conduit is divided into three sections, such as a first section (e.g., an upstream section), a second section (e.g., a center section), and a third section (e.g., a downstream section). As described above, the conduit may have a plurality of nodes that divide the conduit into a number of sections along the length of the conduit.

Including one or more nodes in the conduit may facilitate the detection of when a particle passes through a given segment of the conduit. When transiting the conduit, the particle partially blocks the flow of current across the conduit, leading to a transient increase in the electrical resistance of the conduit. The resulting normalized resistance, or change in current from baseline, is approximately equal to the volume ratio of particle to conduit, i.e., $\delta I/I \sim -V_{particle}/V_{conduit}$. Thus, the change in current depends on the size of the particle relative to the size of the conduit. As described above, the node may have a diameter greater than the diameter of the conduit. As such, when a particle passes from the conduit through a node, a detectable change in current may occur. For example, the resistance may decrease which leads to an increase in the current. In certain instances, the change in current as the particle flows through the nodes in the conduit may facilitate the production of a unique electronic signature that allows for faster real-time analysis and an increase in the precision of the assay.

In certain embodiments, it may be desirable to modify the inner surface of the conduit to reduce or increase the various driving forces (e.g., electroosmotic, electrokinetic, electrophoretic, and the like) through the conduit, or to reduce or increase particle adsorption to the surface of the conduit, and the like. For example, the surface of the conduit may be functionalized to increase particle absorption to the surface of the conduit. The surface of the conduit may be modified to increase particle adsorption to the surface of the conduit to allow for the probing of different molecular interactions. For instance, the surface of the conduit may be modified using silane surface chemistry, allowing molecules to be grafted onto the surface of the conduit. The surface of the conduit may be modified with a coating by using thin-film technology based, for example, on physical vapor deposition, thermal processing, or plasma-enhanced chemical vapor deposition. Alternatively, plasma exposure can be used to directly activate or alter the surface of the conduit and create a functionalized coating on the surface of the conduit. For instance, plasma etch procedures can be used to oxidize a polymeric surface (e.g., polystyrene or polyethylene to expose polar functionalities such as hydroxyls, carboxylic acids, aldehydes, or other reactive moieties).

The coating may include an organic thin film. For instance, an organic thin film may be deposited on the surface by physisorption, spin-coating, chemisorption, self-assembly, plasma-initiated polymerization from the gas phase, and the like. For example, a material such as dextran can serve as a suitable organic thin film. Other thin films include, but are not limited to, lipid bilayers, monolayers of polyarginine or polylysine, self-assembled monolayers, and the like. The coating may cover the whole surface of the conduit or only parts of it. For example, the coating may only be present on the inner surface of the conduit (e.g., the sections of the conduit between the nodes) and may not be present on the inner surface of the nodes. A variety of techniques for generating patterns of coatings on the surface of a support are well known in the art and include, without limitation, microfluidics printing, microstamping, and microcontact printing.

In certain embodiments, the functionalized surface of the conduit may include a binding member. A binding member can be any molecule that specifically binds to a protein or biomacromolecule that is being targeted (e.g., the particle of interest). Depending on the nature of the particle, binding members can be, but are not limited to, (a) antibodies against an epitope of the peptidic particle for the detection of proteins and peptides (or cells which express such proteins or peptides on the cell surface); (b) a protein; (c) a sugar molecule (e.g., a glycan); (d) an aptamer; or (e) any recognition molecule, such as a member of a specific binding pair. For example, suitable specific binding pairs include, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; a member of a peptide aptamer binding pair; a DNA or RNA binding protein; and the like.

In certain embodiments, the binding member includes an antibody. The binding member antibody may specifically bind to a particle of interest. In some cases, the binding member is stably associated with the surface of the conduit. The surface-bound binding member may be configured to specifically bind to the particle of interest. As such, specific binding of the particle of interest to the surface-bound binding member may indirectly bind the particle of interest to the surface of the conduit. Binding of the particle of interest to the surface facilitate detection of the particle of interest. In some instances, the particle is reversibly bound to the binding member, such that the particle is not permanently bound to the binding member. In these instances, the flow of the particle of interest through the conduit may be slowed by reversible binding interactions between the particle and the specific binding member. For example, the particle of interest may be retained in the conduit for a greater amount of time due to reversible binding interactions between the particle of interest and the specific binding member, as compared to the length of time it takes other particles (e.g., particles not specifically bound by the binding member) to flow through the conduit. In some cases, an increase in the amount of time it takes a particle of interest to flow through the conduit may facilitate identifying the particle of interest in a sample. For example, as described above, changes in the current through the conduit are detected to indicate the presence of a particle in the conduit, and as such, an increased retention time in the conduit for a particle of interest may result in a detectable increase in the duration of the change in current.

As described above, the conduit may include one or more nodes that divide the conduit into two or more sections. In certain embodiments, the sections of the conduit include the same functionalized surface. For example, the sections of the conduit may include the same binding member as described above. In other embodiments, the sections of the conduit include different binding members. For instance, a first section of the conduit may include a first functionalized surface that includes a first binding member that specifically binds a first particle, and a second section of the conduit may include a second functionalized surface that includes a second binding member that specifically binds a second particle. Other binding members may be provided in additional sections of the conduit as desired. The use of different binding members in different sections of the conduit may facilitate the detection of different particles of interest in a sample. In some instances, the functionalized surface (e.g., the specific binding members) may only be present on the inner surface of the conduit (e.g., the sections of the conduit between the nodes) and may not be present on the inner surface of the nodes.

In certain embodiments, the conduit is formed in a substrate. For instance, the conduit may be formed as a channel in the substrate. Suitable substrate materials are generally selected based upon their compatibility with the conditions present in the particular operation to be performed by the device. Such conditions can include various pH, temperature, ionic concentration, solvent tolerance and application of electric fields. In certain instances, the substrate material is inert to components of an analysis to be carried out by the device. For example, the substrate material may be selected such that the substrate material does not substantially react with the reagents and/or particles in the samples to be analyzed by the device. Suitable substrate materials include, but are not limited to, glass, quartz, ceramics, and silicon, semiconductor (InAs, GaAs, and the like), as well as polymeric substances, e.g., plastics.

In certain embodiments, the substrate includes a material with a low dielectric constant. For example, the substrate may have a dielectric constant of less than 20, such as less than 15, or less than 10, or less than 5. In some instances, a substrate with a low dielectric constant facilitates a decrease in parasitic capacitance, and thereby facilitates an increase the achievable time resolution.

In the case of polymeric substrates, the substrate materials may be rigid, semi-rigid, or non-rigid, opaque, semi-opaque, or transparent, depending upon the use for which they are intended. For example, devices which include an optical or visual detection element may be used with substrates that are optically transparent materials to facilitate the optical or visual detection. Alternatively, optically transparent windows of glass or quartz, e.g., may be incorporated into the substrate for these types of detection. Optically transparent means that the material allows light of wavelengths ranging from 180 to 1500 nm, such as from 220 to 800 nm, including from 250 to 800 nm, to be transmitted through the material with low transmission losses. Such light transmissive polymeric materials may be characterized by low crystallinity and include polycarbonate, polyethylene terepthalate, polystyrene, polymethylpentene, fluorocarbon copolymers, polyacrylates (including polymethacrylates, such as polymethylmethacrylate (PMMA)), and the like. The polymeric materials may have linear or branched backbones, and may be crosslinked or non-crosslinked. Examples of polymeric materials include, e.g., polydimethylsiloxanes (PDMS), polyurethane, polyvinylchloride (PVC), polystyrene, polysulfone, polycarbonate, polymethylmethacrylate (PMMA) and the like. In certain embodiments, the substrate includes polydimethylsiloxanes (PDMS).

The substrate may additionally be provided with access ports and/or reservoirs for introducing the various fluid elements needed for a particular analysis, as well as outlets for eliminating the various fluids, as described in more detail below.

In certain embodiments, the conduit is formed in the substrate. For example, the substrate may be configured with a conduit passing through the substrate, or a portion of the substrate (e.g., through a central portion of the substrate). In some instances, the conduit may be formed by removing a portion of the substrate (e.g., by drilling, boring, punching, coring, etc. through the substrate). In other instances, the substrate may be formed using a mold that upon removal of the mold leaves a conduit formed through the substrate (or a portion of the substrate as described above). In instances, where the conduit is formed in the substrate itself, a cover (as described in more detail below) may not be needed.

Cover

In certain embodiments, the device includes a cover that overlays the substrate to enclose and fluidically seal channels in the substrate to form the conduit and reservoirs. The cover also include access ports and/or reservoirs for introducing the various fluid elements needed for a particular analysis, as well as outlets for eliminating the various fluids.

The cover may be attached to the substrate by a variety of means, including, e.g., thermal bonding, adhesives, or in the case of certain substrates, e.g., quartz, glass, or polymeric substrates, a natural adhesion between the two components. In some instances, the cover includes an elastomeric material. For example, an elastomeric cover may form a reversible hermetic seal with a smooth planar substrate. Forming a seal in this manner between the substrate and the cover may facilitate removal of the cover from the substrate such that the substrate and the cover may be washed and re-used. Alternatively, the cover may be bonded to the substrate, forming a permanent bond. Forming a permanent bond between the substrate and the cover may facilitate sealing of the cover to the substrate when higher fluid pressures are used. Bonding methods may be used to secure the cap to the substrate, including activating the elastomer surface, for example by plasma exposure, so that the elastomeric cover will bond when placed in contact with the substrate. In certain cases, the cover and substrate are oxidized in a (DC- or AC-generated) oxygen plasma to increase the hydrophilicity of the conduit and to strengthen the seal to the substrate.

The cover may be made from an elastomer, such as, but not limited to, polyisoprene, polybutadiene, polychloroprene, polyisobutylene, poly(styrene-butadiene-styrene), polyurethane, and silicone. Polymers incorporating materials such as chlorosilanes or methyl-, ethyl-, and phenylsilanes, and polydimethylsiloxane (PDMS), or aliphatic urethane diacrylates may also be used. In some cases, the cover is made from materials, such as polyisoprene, polybutadiene, polychloroprene, polyisobutylene, poly(styrene-butadiene-styrene), the polyurethanes, and silicone polymers; or poly(bis(fluoroalkoxy)phosphazene) (PNF, Eypel-F), poly(carborane-siloxanes) (Dexsil), poly(acrylonitrile-butadiene) (nitrile rubber), poly(1-butene), poly(chlorotrifluoroethylene-vinylidene fluoride) copolymers (Kel-F), poly(ethyl vinyl ether), poly(vinylidene fluoride), poly(vinylidene fluoride-hexafluoropropylene) copolymer (Viton), and elastomeric compositions of polyvinylchloride (PVC), polysulfone, polycarbonate, polymethylmethacrylate(PMMA), and polytertrafluoroethylene (Teflon).

In certain embodiments, the thickness of the cover ranges from 0.1 µm to 10 cm, such as from 1 µm to 5 cm, including from 10 µm to 2 cm, or from 100 µm to 10 mm. In some cases, the cover has a thickness of 1 mm to 5 mm, such as 3 mm thick.

Reservoirs

In certain embodiments, the device includes one or more reservoirs, such as one or more fluid reservoirs. The reservoirs may be configured to contain a fluid and/or direct the fluid to or from the conduit. For example, the device may include two reservoirs, such as a first reservoir and a second reservoir. The first reservoir may be in fluid communication with an end of the conduit, such as the upstream end of the conduit. The first reservoir may be configured to contain a fluid (e.g., a sample fluid), and direct the fluid to the upstream end of the conduit. The second reservoir may be in fluid communication with the other end of the conduit, such as the downstream end of the conduit. The second reservoir may be configured to contain the fluid exiting the downstream end of the conduit.

In certain embodiments, the conduit is formed in the substrate as described above. For instance, the conduit may be formed as a channel in the substrate. Applying the cover to the substrate, as described above, may result in the formation of the conduit. Similarly, applying the cover to the substrate may result in two or more enclosed reservoirs connected by the conduit. Each of the reservoirs is adapted to contain a fluid, such as a fluid sample that includes one or more particles. In some instances, the reservoirs have a depth of 5 µm or more, or 10 µm or more, such as 25 µm or more, or 50 µm or more. In certain cases, the reservoirs are configured to contain a fluid volume of 1 µL or more, such as 5 µL or more, including 10 µL or more, or 25 µL or more, or 50 µL or more, or 75 µL or more, or 100 µL or more, or 250 µL or more, or 500 µL or more. In some instances, the reservoirs have the same size and shape. In other embodiments, the reservoirs have different sizes and shapes.

In certain cases, the reservoir includes an inlet port. A fluid sample may be introduced into the reservoirs through the inlet port. In certain instances, the reservoir includes an outlet port. A fluid can be transferred from the reservoirs through the outlet port. A wide range of suitable sizes of inlets and outlets are possible, and those of skill in the art are capable of empirically determining the desired size ranges depending upon the nature of the fluid or the particles to be analyzed. In some cases, the reservoir includes a filter. For example, the reservoir positioned upstream from the conduit may include a filter configured to prevent large particles from clogging the conduit. In other cases, the device does not include a filter. For example, the size of the conduit may be large enough such that the risk of clogging is relatively low.

Detector

In certain embodiments, the device includes a detector. The detector may be configured to detect a change in current through the conduit. For example, the detector may be configured to measure the change in resistance (e.g., for a DC device) or impedance (e.g., for an AC device) of the conduit with the passage of each particle therethrough. In certain instances, the detector includes two or more electrodes. For instance, the detector may be a two-point (e.g., two-electrode) detector, a three-point (e.g., three-electrode) detector, a four-point (e.g., four-electrode) detector, and the like.

In certain embodiments, the detector is configured to quantify the uncompensated electrical resistance (e.g., extraneous resistance that is in series with the conduit resistance) arising from the fluid leading to the conduit. Thus, in some embodiments, the detector includes a four-point (e.g., four-electrode) detector having two inner electrodes and two outer electrodes. In some cases, the outer electrodes pass a constant current into the solution in the conduit, and the inner electrodes are used to measure changes in voltage. In other instances, the inner electrodes hold a constant voltage, while the outer electrodes are configured to measure changes in current. In certain embodiments, the outer electrodes are configured to pass a current into the solution, whereas the inner electrodes control the voltage applied to the conduit, but pass no current.

In certain embodiments, the electrodes are disposed on the substrate. For example, the electrodes can be made by depositing metal onto the surface of the substrate. The electrodes (and their respective connections to the signal detector) can include any biocompatible substance such as, but not limited to, gold, silver, titanium, copper, platinum, iridium, polysilicon, carbon, aluminum, and the like. In certain instances, the electrodes include titanium and platinum, or titanium and silver.

The electrodes may be configured to be symmetric and equidistant from the conduit. The inner electrodes may be positioned proximate to the conduit. In some embodiments, the electrodes may be positioned at a distance from the conduit of 500 µm or less, such as 250 µm or less, or 100 µm or less, including 75 µm or less, or 50 µm or less, or 25 µm or less, or 10 µm or less. In some embodiments, when uncompensated resistance arising from the fluid in the reservoir is small (for example, when the reservoirs are wide and deep compared to the conduit), the placement of the inner electrodes may be greater. For example, in some circumstances, the inner electrodes can be positioned 1 mm or more from the conduit.

The detector can be configured to measure a change in impedance, resistance or current. The residence time of a particle in the conduit can be measured simultaneously with the measurement of the change in current. In some cases, the detector is also configured to measure the effects of voltage on the current. For example, different voltages may be applied during an assay to determine if the change in current scales linearly with the voltage. In some cases, the state of some particles may change with an applied electric field. As the electric field varies with voltage, varying the voltage may provide information about the state of the particles. Such information may relate to conformational changes of a large, flexible molecule, changes of the effective charge of a particle due to the applied field affecting the counter-ion layer around the particle, and the like. In addition, a particle with a dipole moment may become more stringently aligned to a large electric field, which may change the range of peak sizes measured for the particle.

The detector may utilize either AC or DC current. For embodiments of the detector that use AC current, the phase as well as the current may be measured. In some cases, frequencies of 10 kHz or more, such as 15 kHz or more, or 20 kHz or more, or 25 kHz or more, or 30 kHz or more, or 35 kHz or more, or 40 kHz or more, or 45 kHz or more, or 50 kHz or more may be measured. This technique may facilitate the differentiation between particles based on charge.

In certain embodiments, the device is configured to detect particles of a size large enough to cause a detectable change in current as the particle passes through the conduit. For example, the device (including the detector) may be configured to detect micro-scale or nano-scale sized particles. By micro-scale is meant particles that have a size (e.g., average diameter) ranging from 1 to 1000 µm. By nano-scale is meant particles that have a size (e.g., average diameter) ranging from 1 to 1000 nm. For example, the device may be configured to detect a particle with an average size of 100 µm or less, or 50 µm or less, such as 25 µm or less, or 20 µm or less, or 15 µm or less, or 10 µm or less, or 5 µm or less, or 3 µm or less, or 1 µm or less, or 900 nm or less, or 800 nm or less, or 700 nm or less, or 600 nm or less, or 500 nm or less, or 400 nm or less, or 300 nm or less, or 200 nm or less, or 100 nm or less, or 50 nm or less, or 25 nm or less, or 10 nm or less, or 5 nm or less, or 1 nm or less. In some instances, the device has a range of detection for particles with sizes ranging from 1 nm to 100 µm, such as from 10 nm to 50 µm, including from 25 nm to 25 µm, or from 50 nm to 20 µm, or from 100 nm to 15 µm.

FIG. 1(panel a) shows an image of a device that includes a conduit with two nodes and electrodes to perform a resistive-pulse reading. The device 10 includes a first reservoir 20 and a second reservoir 30, separated by a conduit 40. The conduit 40 includes two nodes, a first node 50 and a second node 60, which separate the conduit 40 into three sections, 70, 80 and 90, respectively. FIG. 1(panel b) shows a graph of the corresponding transient three-pulse current reading as a particle passes through the three sections of the conduit. As shown in the graph, the current decreases from the baseline current when a particle passes through section 70 of the conduit, increases as the particle passes through node 50, decreases as the particle passes through section 80 of the conduit, increases as the particle passes through the node 60, decreases as the particle passes through section 90 of the conduit, and increases back to baseline when the particle exits the conduit.

Methods

Aspects of embodiments of the present disclosure include a method of detecting a particle in a fluid sample. The method includes passing a fluid sample that includes a particle through a microfluidic conduit, and applying a current through the conduit to produce a detectable signal that corresponds to the presence of the particle in the conduit. As described above, the conduit includes one or more nodes positioned along the conduit dividing the conduit into two or more sections.

Embodiments of the methods are directed to determining whether a particle is present in a sample, e.g., determining the presence or absence of one or more particles in a sample. In certain embodiments of the methods, the presence of one or more particles in the sample may be determined qualitatively or quantitatively. Qualitative determination includes determinations in which a simple yes/no result with respect to the presence of a particle in the sample is provided to a user. Quantitative determination includes both semi-quantitative determinations in which a rough scale result, e.g., low, medium, high, is provided to a user regarding the amount of particle in the sample and fine scale results in which an exact measurement of the concentration of the particle is provided to the user.

In certain embodiments, the device is configured to detect the presence of one or more particles in a sample. For example, the device may be configured to have a detection limit of one particle per sample (e.g., the device is able to detect a single particle is a given sample). In some cases, the device is configured to have a detection limit of 1000 particles per sample or less, such as 900 particles per sample or less, including 800 particles per sample or less, or 700 particles per sample or less, or 600 particles per sample or less, or 500 particles per sample or less, or 400 particles per sample or less, or 300 particles per sample or less, or 250 particles per sample or less, or 200 particles per sample or less, or 150 particles per sample or less, or 100 particles per sample or less, or 75 particles per sample or less, or 50 particles per sample or less, or 25 particles per sample or less, or 20 particles per sample or less, or 15 particles per sample or less, or 10 particles per sample or less, or 5 particles per sample or less, or 4 particles per sample or less, or 3 particles per sample or less, or 2 particles per sample or less, or 1 particle per sample.

Samples that may be assayed with the subject microfluidic devices may vary, and include both simple and complex samples. Simple samples are samples that include the particle of interest, and may or may not include one or more molecular entities that are not of interest, where the number of these non-interest molecular entities may be low, e.g., 10 or less, 5 or less, etc. Simple samples may include initial biological or other samples that have been processed in some manner, e.g., to remove potentially interfering molecular entities from the sample. By "complex sample" is meant a sample that may or may not have the particles of interest, but also includes many different proteins and other molecules that are not of interest. In some instances, the complex sample assayed in the subject methods is one that includes 10 or more, such as 20 or more, including 100 or more, e.g., $10^3$ or more, $10^4$ or more (such as 15,000; 20,000 or 25,000 or more) distinct (i.e., different) molecular entities, that differ from each other in terms of molecular structure or physical properties (e.g., molecular weight, size, charge, isoelectric point, etc.).

In certain embodiments, the samples of interest are biological samples, such as, but not limited to, urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue, and the like. The sample can be a biological sample or can be extracted from a biological sample derived from humans, animals, plants, fungi, yeast, bacteria, tissue cultures, viral cultures, or combinations thereof using conventional methods for the successful extraction of proteins and peptides. In certain embodiments, the sample is a fluid sample, such as a solution of particles in a fluid. The fluid may be an aqueous fluid, such as, but not limited to water, a buffer, and the like.

As described above, the samples that may be assayed in the subject methods may include one or more particles of interest. Examples of detectable particles include, but are not limited to: cells, viruses; proteins and peptides (e.g., proteins and peptide expressed on the surface of cells and/or viruses), with or without modifications, e.g., antibodies, diabodies, Fab fragments, binding proteins, phosphorylated proteins (phosphoproteomics), peptide aptamers, epitopes, DNA, RNA, and the like.

In certain instances, the method includes detecting the signal to determine the presence of the particle in the conduit. When transiting the conduit, a particle partially blocks the flow of current across the conduit, leading to a transient increase in the electrical resistance of the conduit (and thus a decrease in the current). Detection of the change in resistance (or impedance or current) in the conduit indicates the presence of the particle in the conduit. Because detection of the particle of interest is based on changes in current (rather than, for example fluorescence-based detection techniques), in some embodiments, the particles are not labeled prior to passing the sample through the conduit. In some cases, the method further includes quantifying the number of particles that pass through the conduit. For instance, the number of particles of interest may be counted as the particles of interest flow through the conduit. Particles not of interest are not significantly included in the quantification of the particles of interest.

In certain embodiments, the method includes characterizing the particle as the particle passes through the conduit. A variety of characteristics about the particle may be characterized by the device. For example, characterizing the particle may include determining the size of the particle, such as the average diameter of the particle. In some instances, determining the size of a particle includes measuring the current across the conduit connected to two reservoirs. As described above, when transiting the conduit, the particle partially blocks the flow of current across the conduit, leading to a transient increase in the electrical resistance of the conduit. The resulting normalized resistance, or change in current from baseline, is approximately equal to the volume ratio of particle to conduit, i.e., $\delta I/I \sim V_{particle}/V_{conduit}$. Thus, the magnitude of the change in current depends on the size of the particle. As such, the method may include determining the size of the particle based on the change in current measured during an assay.

In some cases, characterizing the particle includes determining the type of particle that is passing through the conduit. For instance, a surface characteristic of the particle of interest may be determined, such as whether a particular biomarker is present on the surface of the particle. In these embodiments, the method may include determining whether a biomarker is present on the particle based on the detected signal. As described above, sections of the conduit may include a functionalized surface, such as a surface that includes a binding member (e.g., an antibody). As described above, the particle of interest may be retained in the conduit for a greater amount of time due to reversible binding interactions between the particle of interest and the specific binding member, as compared to the length of time it takes other particles (e.g., particles not specifically bound by the binding member) to flow through the conduit. In these embodiments, the method may include determining whether a biomarker is present on the particle based on the duration of the change in current. For example, a change in current with a greater duration may indicate specific binding interactions between the particle and the specific binding member on the surface of the conduit, and thus indicates the presence of a specific biomarker on the particle.

In certain embodiments, characterizing the particle includes determining the dynamics of the particle over time. For example, as discussed above, when transiting the conduit, the particle partially blocks the flow of current across the conduit, leading to a transient increase in the electrical resistance of the conduit. In some cases, the magnitude of the change in current depends on the orientation of the particle with respect to the conduit. For instance, a particle that is not spherical may have a first cross sectional area that is greater than a second cross sectional area of the particle. As the particle traverses the conduit, the particle may rotate such that the cross sectional area of the particle with respect to the cross sectional area of the conduit changes over time. In certain cases, changes in the ratio of the cross sectional area of the particle to the cross sectional area of the conduit may be detected and the dynamics of the particle over time may be determined.

Figure 8:
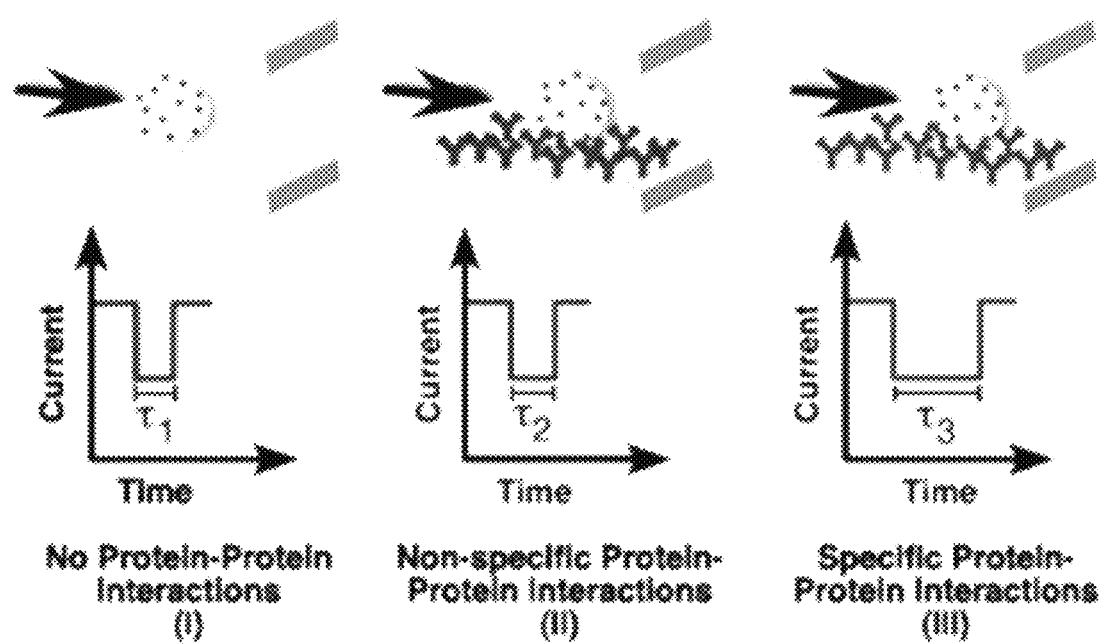
FIG. 8 shows schematics of a device used to determine the presence of surface biomarkers on a cell, according to embodiments of the present disclosure.

For example, as shown in FIG. 8, the presence of surface biomarkers on the cell can be determined by recording the transit time of the cell as it transits a conduit that has no antibodies functionalized on the surface (FIG. 8(I)), control antibodies functionalized (FIG. 8(II)), or specific antibodies functionalized on the surface (FIG. 8(III)). Specific interactions between the cell surface biomarker and the specific antibodies (FIG. 8(III)) will cause the cell to travel more slowly through the conduit than when there are no interactions or non-specific interactions (FIGS. 8(I) and 8(II), respectively. Transit time is determined by the pulse width of the current pulse caused by the cell passing through the conduit. In FIG. 8, tau(3)>tau(2)>tau(1), and so the cell is positive for the cell surface biomarker in FIG. 8(III).

In certain embodiments, the particle of interest is detected and characterized in real-time. By "real-time" is meant that the detection and characterization of the particle of interest occurs as the signal from the particle passing through the conduit is generated. For example, the detected signal is not stored and then analyzed at a later point in time to determine the presence and characterization of the particle. In other embodiments, the detected signals are stored and analyzed at a later point in time. For example, data from several assays may be stored and analyzed together at a later point in time.

In certain instances, particles to be detected and characterized are suspended at an appropriate concentration in a suitable liquid medium, e.g., a fluid sample. The fluid sample may have an electrical impedance per unit volume that differs from that of the particles to be characterized. Any suitable liquid media (either aqueous or nonaqueous) that includes ionic species may be used in the devices and methods disclosed herein. For example, liquid media such as, but not limited to, water, organic solvents, cell cultures, animal or human bodily fluids, solutions including particles and/or biological molecules, cellular cytoplasm, cellular extracts, cellular suspensions, solutions of labeled particles or biological molecules, solutions including liposomes, encapsulated material, or micelles, etc. may be used.

The fluid sample may also include the particles to be detected, which can include live cells, parts of cells such as ribosomes or nuclei, and/or macromolecules such as proteins or fragments thereof. Particles may be any material capable of causing a change in an electrical characteristic (e.g., resistance, impedance, current, etc.) of the conduit when the fluid comprising the particles flows through the conduit. By way of example, but not by way of limitation, particles may also include any polymer particle, such as polystyrene beads, latex beads, colloids (e.g., metal colloids), magnetic particles, dielectric particles, crystals (e.g., micro-crystals or nano-crystals), bioparticles such as pores, pollen, cellular occlusions, precipitates, intracellular crystals, and biological molecules, including viruses, polysaccharides, polypeptides, proteins, lipids, peptidoglycans, and any other cellular components.

The particles may be positively or negatively charged, or even neutral. As such, a variety of driving mechanisms may be used to produce a flow of the sample fluid through the device. For example, electrophoretic, electrokinetic or electroosmotic forces, or pressure gradients may be used. In some instances, the method includes applying a pressure to the fluid to provide a flow of the fluid through the device. Other embodiments may include pumping the fluid through the device to provide a flow of the fluid through the device. The rate of flow in delivering the fluid sample to the device may be selected to allow sufficient time for the device to detect and/or measure the electrical characteristic(s) of the particle to be measured. For example, the flow rate may be 0.1 µL/min or more, such as 0.5 µL or more, or 1 µL or more, or 2 µL or more, or 3 µL or more, or 4 µL or more, or 5 µL or more, or 6 µL or more, or 7 µL or more, or 8 µL or more, or 9 µL or more, or 10 µL or more.

In some embodiments, the methods include the uniplex analysis of a particle in a sample. By "uniplex analysis" is meant that a sample is analyzed to detect the presence of one particle in the sample. For example, a sample may include a mixture of a particle of interest and other molecular entities that are not of interest. In some cases, the methods include the uniplex analysis of the sample to determine the presence of the particle of interest in the sample mixture. For example, as described above, a conduit may include a functionalized surface that includes one type of antibody specific for a single particle.

Certain embodiments include the multiplex analysis of two or more particles in a sample. By "multiplex analysis" is meant that the presence two or more distinct particles, in which the two or more particles are different from each other, is determined. For example, particles may include detectable differences in surface biomarkers. In some instances, the number of particles is greater than 2, such as 4 or more, 6 or more, 8 or more, etc., up to 20 or more, e.g., 50 or more, including 100 or more, distinct particles. In certain embodiments, the methods include the multiplex analysis of 2 to 100 distinct particles, such as 4 to 50 distinct particles, including 4 to 20 distinct particles.

Figure 9:
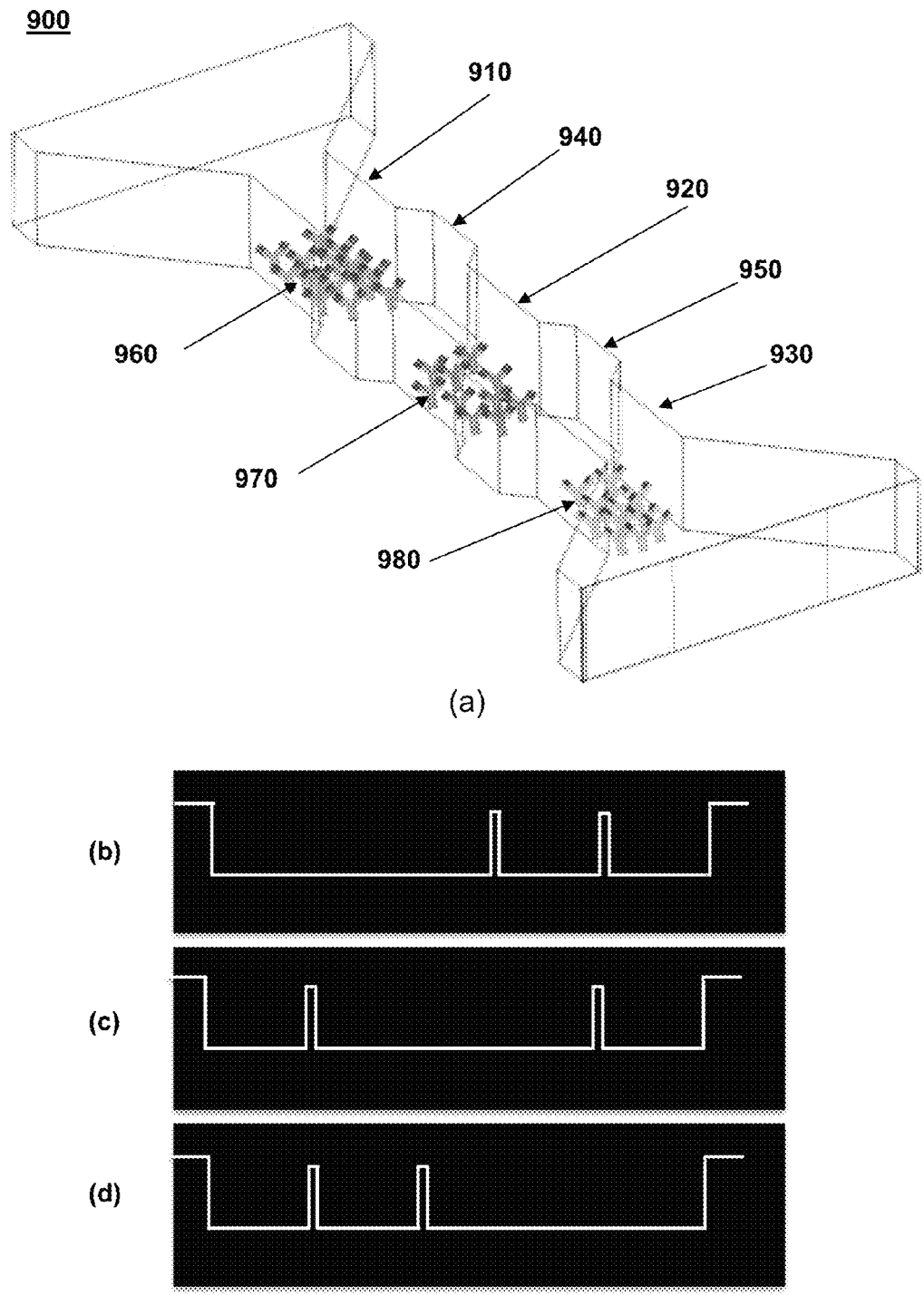
FIG. 9 shows a schematic of a device and corresponding current signal of a device configured for multiplex analysis, according to embodiments of the present disclosure.

For example, FIG. 9 shows the multiple analysis of a sample for 3 different particles. As shown in FIG. 9(panel a), in the device 900, the conduit is divided into three different sections (e.g., a first section 910, a second section 920, and a third section 930) by two nodes (e.g., a first node 940 and a second node 950). Each section between nodes is functionalized with a different antibody corresponding to a different surface epitope. First section 910 is functionalized with first antibody 960, second section 920 is functionalized with second antibody 970, and third section 930 is functionalized with third antibody 980. Cells transit the different channels and the current pulse is subdivided per the number of sections in the channel. Different transit times can be compared within the sections. As shown in FIG. 9(panel b), cells with biomarkers specific to the first antibody 960 slow down in the first section 910 of the conduit and this is reflected in the longer duration first current pulse in FIG. 9(panel b). As shown in FIG. 9(panel c), cells with biomarkers specific to the second antibody 970 slow down in the second section 920 of the conduit and this is reflected in the longer duration second current pulse in FIG. 9(panel c). As shown in FIG. 9(panel d), cells with biomarkers specific to the third antibody 970 slow down in the third section 930 of the conduit and this is reflected in the longer duration third current pulse in FIG. 9(panel d).

In certain embodiments, the method further includes sorting the particles. For example, the device may be configured to separate particles once those particles have passed through the conduit. In this regard, methods of the present disclosure may be used for fractionating large biological molecules such as proteins, or fractionating colloids or particles which are attached to proteins.

In addition, the devices can be used as a component of a sorting system. As such, the methods may include detecting the sizes of particles as they pass through the conduit. Particles of a selected size (or range of sizes) can be directed along one flow path (e.g., through a first set of channels) for further processing while particles of other sizes can be directed along a different flow path (e.g., through a second set of channels). Similarly, in embodiments of the devices that include a functionalized surface as described above, the method may include separating particles of a selected size and of a specified type (e.g., particles with a specific biomarker) from those having either a different size and/or of a different type (e.g., with a different biomarker).

Methods of the present disclosure also include methods of fabricating the devices described herein. The conduit can be formed by a variety of methods. In some embodiments, the conduit is etched into a substrate which is then sealed by a cover (e.g., an elastomeric cover). In other embodiments, the conduit can be molded into the cover (e.g., the elastomeric cover) which is then laid on top of the substrate.

Manufacturing of devices may be carried out by any number of microfabrication techniques. For example, lithographic techniques may be employed in fabricating glass, quartz or silicon substrates, for example, with methods known in the semiconductor manufacturing industries. Photolithographic masking, plasma or wet etching and other semiconductor processing technologies may be used to define microscale elements in and on substrate surfaces. Alternatively, micromachining methods, such as laser drilling, micromilling and the like, may be employed. Similarly, for polymeric substrates, manufacturing techniques such as, but not limited to, injection molding techniques or stamp molding methods may be used. In some cases, large numbers of substrates may be produced using, e.g., rolling stamps to produce large sheets of microscale substrates, or polymer microcasting techniques where the substrate is polymerized within a microfabricated mold.

Two exemplary methods of fabricating the present invention are provided herein. It is to be understood that the present invention is not limited to fabrication by one or the other of these methods. Rather, other suitable methods of fabricating the present devices, including modifying the present methods, are also contemplated. One method involves a series of lithographic processes in which the reservoirs and conduit are etched into a planar substrate. These methods can be used to make a large number of devices on a single chip, thus increasing efficiency through parallelization. The second method involves producing a conduit and reservoirs in an elastomeric cover which is then contacted with the substrate.

Systems

Aspects of the present disclosure include a system for detecting a particle in a fluid sample. The system includes a device for detecting a particle in a fluid sample, as described herein. As described above, the device includes a microfluidic conduit configured to carry a flow of a fluid sample, where the conduit includes one or more nodes positioned along the conduit dividing the conduit into two or more sections. The system further includes a detector configured to detect a change in current through the conduit, as described in detail above.

The systems of the present disclosure may further include a fluid deliver system, such as a microfluidic or nanofluidic fluid delivery system. Microfluidic fluid delivery systems may include systems where the total volume of biological solution at any one time is 1000 microliters or less. Nanofluidic fluid delivery systems may include systems where the total volume of biological solution at any one time is 1000 nanoliters or less. The fluid deliver system may include one or more pumps configured to provide a flow of a fluid through the device.

Aspects of the presently disclosed system also provide for an integrated "chip" having one or more microfluidic devices for detecting and measuring particles. In certain embodiments, the chip includes a plurality of devices for detecting particles, such as 2 or more devices, or 4 or more devices, or 6 or more, or 8 or more, or 10 or more devices. The two or more devices may be arranged in series (e.g., with a first device positioned upstream from a second device) or in parallel (e.g., with a first and second devices arranged in parallel).

In some instances, the systems include a sorter configured to sort such identified particles, where the integrated chip identifies and sorts particles of interest. For example, the integrated chip is configured to sort a mixture of cells, polynucleotides or proteins, or any other particle or biological molecule of interest. In some instances, the sorter is in fluid communication with the device and is positioned downstream from the device.

In certain embodiments, upstream from the device may be included one or more of a filtration system, a dilution system, and a system to adjust the driving force of the medium. The system may also include an optical detection device for further analytical applications, such as for multiplexed assays or analysis of heterogeneous mixtures. For example, fluorescence of the various particles may be detected as well as the size and type of particle, as described above.

Additional aspects of the devices, methods and systems are described further in U.S. Pat. No. 7,279,883, the disclosure of which is incorporated herein by reference in its entirety.

Utility

The subject devices, systems and methods find use in a variety of different applications where determination of the presence or absence, and/or quantification of one or more particles in a sample is desired. In certain embodiments, the methods are directed to the detection of cells, viruses, proteins, or other biomolecules in a sample. The methods may include the detection of a biomarker, e.g., one or more distinct protein biomarkers, in a sample. For example, the methods may be used in the rapid, clinical detection of one or more disease biomarkers in a biological sample, e.g., as may be employed in the diagnosis of a disease condition in a subject, in the ongoing management or treatment of a disease condition in a subject, etc. In addition, the subject devices, systems and methods may find use in protocols for the detection of a particle in a sample for sorting particles of interest from other components of the sample.

In certain embodiments, the subject devices, systems and methods find use in detecting biomarkers. In some cases, the subject devices, systems and methods may be used to detect the presence or absence of particular biomarkers, as well as an increase or decrease in the concentration of particular biomarkers in blood, plasma, serum, or other bodily fluids or excretions, such as but not limited to urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue, and the like.

The presence or absence of a biomarker or significant changes in the concentration of a biomarker can be used to diagnose disease risk, presence of disease in an individual, or to tailor treatments for the disease in an individual. For example, the presence of a particular biomarker or panel of biomarkers may influence the choices of drug treatment or administration regimes given to an individual. In evaluating potential drug therapies, a biomarker may be used as a surrogate for a natural endpoint such as survival or irreversible morbidity. If a treatment alters the biomarker, which has a direct connection to improved health, the biomarker can serve as a surrogate endpoint for evaluating the clinical benefit of a particular treatment or administration regime. Thus, personalized diagnosis and treatment based on the particular biomarkers or panel of biomarkers detected in an individual are facilitated by the subject devices, systems and methods. Furthermore, the early detection of biomarkers associated with diseases is facilitated by the high sensitivity of the subject devices and systems. Due to the capability of detecting multiple biomarkers on a single chip, combined with sensitivity, scalability, and ease of use, the presently disclosed devices, systems and methods finds use in portable and point-of-care or near-patient molecular diagnostics.

In certain embodiments, the subject devices, systems and methods find use in detecting biomarkers for a disease or disease state. In some cases, the disease is a cellular proliferative disease, such as but not limited to, a cancer, a tumor, a papilloma, a sarcoma, or a carcinoma, and the like. In certain instances, the subject devices, systems and methods find use in detecting biomarkers for the characterization of cell signaling pathways and intracellular communication for drug discovery and vaccine development. For example, the subject devices, systems and methods find use in detecting the presence of a disease, such as a cellular proliferative disease, such as a cancer, tumor, papilloma, sarcoma, carcinoma, or the like. In certain instances, particular biomarkers of interest for detecting cancer or indicators of a cellular proliferative disease include For example, the subject devices, systems and methods may be used to detect and/or quantify acute promylocytic leukemia (APL) in a subject. Rapid diagnosis of APL may facilitate earlier administration of treatment protocols to the subject. For example, the subject devices and methods may have an assay time of 15 minutes or less, such as 10 minutes or less, or 7 minutes or less, or 5 minutes or less, or 3 minutes or less, or 2 minutes or less, or 1 minute or less. The subject devices, systems and methods also find use in isolating and screening circulating tumor cells (CTCs) in a subject. In some instances, quantification of CTC levels in a subject may facilitate evaluation and tracking of metastatic progression in the subject. The subject devices, systems and methods may also be used to screen CTCs for specific surface biomarkers, which may facilitate the characterization of the particular CTCs in the subject.

In certain embodiments, the subject devices, systems and methods find use in detecting biomarkers for an infectious disease or disease state. In some cases, the biomarkers can be molecular biomarkers, such as but not limited to proteins, carbohydrates, small molecules, and the like. For example, the subject devices, systems and methods may be used to monitor HIV viral load and patient CD4 count for HIV/AIDS diagnosis and/or therapy monitoring by functionalizing the sensor surface with antibodies to HIV capsid protein p24, glycoprotiens 120 and 41, CD4+ cells, and the like. Particular diseases or disease states that may be detected by the subject devices, systems and methods include, but are not limited to, bacterial infections, viral infections, increased or decreased gene expression, chromosomal abnormalities (e.g. deletions or insertions), and the like.

The subject device, systems and methods find use in diagnostic assays, such as, but not limited to, the following: detecting and/or quantifying biomarkers, as described above; screening assays, where samples are tested at regular intervals for asymptomatic subjects; prognostic assays, where the presence and or quantity of a biomarker is used to predict a likely disease course; stratification assays, where a subject's response to different drug treatments can be predicted; efficacy assays, where the efficacy of a drug treatment is monitored; and the like.

The subject devices, systems and methods also find use in validation assays. For example, validation assays may be used to validate or confirm that a potential disease biomarker is a reliable indicator of the presence or absence of a disease across a variety of individuals. The short assay times for the subject devices, systems and methods may facilitate an increase in the throughput for screening a plurality of samples in a minimum amount of time.

In some instances, the subject devices, systems and methods can be used without requiring a laboratory setting for implementation. In comparison to the equivalent analytic research laboratory equipment, the subject devices and systems provide comparable analytic sensitivity in a portable, hand-held system. In some cases, the weight and operating cost are less than the typical stationary laboratory equipment. The subject systems and devices may be integrated into a single apparatus, such that all the steps of the assay, including detection and sorting of a particle of interest, may be performed by a single apparatus. In addition, the subject systems and devices can be utilized in a home setting for over-the-counter home testing by a person without medical training to detect one or more particles in samples. The subject systems and devices may also be utilized in a clinical setting, e.g., at the bedside, for rapid diagnosis or in a setting where stationary research laboratory equipment is not provided due to cost or other reasons.

Kits

Aspects of the present disclosure additionally include kits that have a device as described in detail herein. The kits may further include a buffer. For instance, the kit may include a buffer, such as a sample buffer, a wash buffer, and the like. The kits may further include additional reagents, such as but not limited to, detectable labels (e.g., fluorescent labels, colorimetric labels, chemiluminescent labels, multicolor reagents, enzyme-linked reagents, avidin-streptavidin associated detection reagents, radiolabels, gold particles, magnetic labels, etc.), and the like.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Another means would be a computer readable medium, e.g., CD, DVD, Blu-Ray, computer-readable memory, etc., on which the information has been recorded or stored. Yet another means that may be present is a website address which may be used via the Internet to access the information at a removed site. Any convenient means may be present in the kits.

As can be appreciated from the disclosure provided above, embodiments of the present invention have a wide variety of applications. Accordingly, the examples presented herein are offered for illustration purposes and are not intended to be construed as a limitation on the invention in any way. Those of ordinary skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

EXAMPLES

Introduction

When transiting a conduit, a particle partially blocks the flow of current across the conduit, leading to a transient increase in the electrical resistance of the conduit. The resulting normalized resistance, or change in current from baseline, is approximately equal to the volume ratio of particle to conduit, i.e. $\delta I/I \sim -V_{particle}/V_{conduit}$. While single current pulses may be hidden within noise, the unique electronic signatures produced by the devices of the present disclosure facilitate signal extraction. Experiments were performed showing measurements with $V_{particle}/V_{conduit}$ of $1.2 \times 10^{-9}$ for screening nanoscale particles with microscale devices. Devices with low $V_{particle}/V_{conduit}$ reduce the possibility of clogging that can occur in low $V_{conduit}$ devices.

General Experimental Protocol

Fabrication of Device Masters on Silicon Wafers

Photolithography is used to pattern silicon wafers with designs corresponding to desired devices.

A silicon wafer was placed on a spinner. SU-8 2025 photoresist was poured onto the wafer until it spread to the size of a quarter (~25 mm diameter). Based on SU-8 spin curves, the wafer was spun at speed for the desired height of the conduit (this protocol created masters that had 100 μm high reservoirs and 25 μm high conduits). The spin speed was 3000 rpm, and spinning took place for at least a minute. Conduit size was typically 800 μm×25 μm×25 μm (L×W×H), but conduit and reservoir size can be tuned for each specific application.

The wafer was placed on a hot plate at 65° C. for 1 minute and then at 95° C. for 5 minutes. The wafer was cooled and then UV exposed with device conduit mask. Exposure occurred at 275 W for 22 seconds. The wafer was placed on a hot plate at 65° C. for 1 minute and at 95° C. for 5 minutes. The wafer was cooled and developed in SU-8 Developer for 4 minutes. The wafer was washed with isopropanol and observed for white film during rinse. If white film was present, the wafer was returned to developer and the rinse step was repeated until the film dissolved. To strengthen the properties of the resist, a hard bake was performed, ramping the temperature from 100° C. to 150° C. over five minutes. The temperature was held at 150° C. for an hour.

The patterned silicon wafer was placed on a spinner. SU-8 2100 photoresist was poured onto the wafer until it spread to the size of a quarter (~25 mm diameter). Based on SU-8 spin curves, the wafer was spun at speed for desired height of reservoir (this protocol created masters that had 100 μm high reservoirs and 25 μm high conduits). The reservoir spin speed was 3000 RPM, and spinning took place for at least a minute.

The wafer was placed on a hot plate at 65° C. for 5 minutes and then at 95° C. for 20 minutes. The wafer was cooled and then UV exposed with device reservoir mask. The reservoir mask was aligned properly with the conduit resist pattern such that the conduit connected the two reservoirs. Exposure was at 275 W for 70 seconds.

The wafer was placed on a hot plate at 65° C. for 5 minutes and at 95° C. for 10 minutes. The wafer was cooled developed in SU-8 Developer for 10 minutes. The wafer was washed with isopropanol and observed for white film during rinse. If white film was present, the wafer was returned to developer and the rinse step was repeated until the film dissolved. To strengthen the properties of the resist, a hard bake was performed from 100° C. ramped up to 150° C. over five minutes. The temperature was held at 150° C. for an hour.

PDMS Molds of Microfluidic Channels

PDMS was poured onto the patterned silicon wafers with negative masters to form PDMS molds of microchannels.

Dow Corning Sylgard 184 Base was mixed with Curing Agent in 10:1 ratio (30 g Base: 3 g Curing Agent for a 3 inch diameter wafer) in a cup. The cup with PDMS mixture was placed in a vacuum desiccator until fully degassed. The mixture was poured onto the wafer in a petri dish and placed on a hot plate at 80° C. for 45 minutes. The petri dish was removed from the hot plate and molds/devices was cut out using a knife.

Fabrication of Electrodes

Electrodes were patterned onto glass substrates.

Shipley S1813 photoresist was spun on a glass slide at 3000 RPM for 60 seconds. The slide was baked on a hot plate at 110° C. for 1 minute. The glass slide was exposed to UV at 275 W for 25 seconds. The glass slide was developed in MF 321 Developer for 70 seconds. The slide was washed thoroughly with DI water. The slide was dried. The glass slides were loaded into a thin-film electron-gun evaporator and 75 Å Ti, 250 Å Pt, and 250 Å Au was deposited. The glass slides were placed in acetone for 30 minutes for liftoff. 30 μL of Gold etchant was pipetted onto electrodes (not the contact pads) and etched for 30 seconds before rinsing with DI water.

RCA Clean Electrode Slides

Electrodes slides were cleaned prior to microchannel bonding.

Glass slides were placed in a beaker with a 5:1 mixture of DI water and $NH_4OH$ and heated at 150° C. for 30 minutes. $H_2O_2$, 30% (in the same volume as $NH_4OH$ added) was added and allowed to bubble for 15 minutes. The slides were rinsed in DI water, dried, and stored in methanol for further use.

Silanization of Glass Substrates

Glass substrates were silanized in the regions that formed the conduit.

10 μl of 2:1 methanol: water was placed onto the glass substrate and a temporary PDMS channel (cored for entry and exit ports) was aligned perpendicular to conduit alignment so that the only region of intersection was the conduit. The glass substrate was placed on a hot plate at 120° C. for 20 minutes to create a temporary bond. The substrate was cooled and temporary bonded channels were filled with 1M NaOH and allowed to sit for 10 minutes. The channels were rinsed with DI water and dried on a hot plate at 150° C. for 10 minutes. The channels were cooled and stock and silane solutions were prepared. Stock solution was 95% 200 proof ethanol with 4.999% HPLC Grade water and 0.001% Glacial Acetic Acid. Stock solution was reusable. Silane solution was made with 4.9 mL stock solution and 0.1 mL N-3-triethoxysilypropyl-4-hydroxybutramide or APTES.

The channels were filled with silane solution and incubated in a humid chamber with ethanol for 4 hours. The channels were checked after 2 hours to make sure channels were still filled with silane solution and refilled if necessary. The channels were filled with stock solution for 20 minutes. The temporary-bonded channels were removed and the glass substrate was rinsed with DI water, air dried, and placed on a hot plate at 120° C. for 2 hours.

Plasma Bonding

PDMS molds of conduit devices were bonded to silanized glass substrates.

PDMS molds of conduit devices were cored for entry and exit ports using a 16-gauge syringe needle. PDMS molds were placed with channels face up onto a glass slide, and Scotch tape was applied and removed on the surface in order to clean prior to bonding. PDMS guards were cut to cover the silanized region of the electrode slides that were bonded to the conduit area. Oxygen plasma (200 mTorr, 80 W) was applied to the PDMS molds and electrode slides. The PDMS guards were removed, and 10 µl of 2:1 methanol: water was applied on the glass substrate and the PDMS mold was aligned and placed with conduit face down. The device was placed on a hot plate at 50° C. and the temperature was ramped up to 120° C. for 45 minutes.

Antibody Functionalization

Antibody was functionalized onto the glass substrate in the region of the conduit.

Sulfo-EGS mixture (4:1 Sulfo-EGS: PBS) was added to devices. The devices were incubated in a humid chamber for 20 minutes. DI water was added to the devices before flushing through with air. Protein G or L (1 mg/mL Protein G: PBS or 7.66 mg/mL Protein L: PBS) was added to the devices. The devices were incubated in a humid chamber for at least 4 hours. The devices were flushed with DI water through the devices before flushing through with air. Antibody at 0.25 mg/mL (dilute in PBS) was added. The devices were incubated for at least 4 hours in a humid chamber at room temperature. The devices were stored at 4° C. for long incubations.

Pulse Measurement

Depending on the electronics used, electrodes were connected to the measurement setup. Supply voltage was connected at the desired level, and current measurement probes were connected to an amplifier or measurement instrumentation. A four-point measurement of the current was made using a constant applied AC voltage (0.2-0.4 V). The current was passed through a preamplifier (DL Instrument 1211) that applied a low-pass filter at 0.3 ms in rise time. The resulting output was connected to a data acquisition board (National Instruments PCI-6035E) for data sampling (50 kHz). A sample was inserted using tubing into the cored entry port. Pressurized air (0.25-5 psi) was connected to the entry port tubing and measurement was begun.

Device Design

Figure 2:
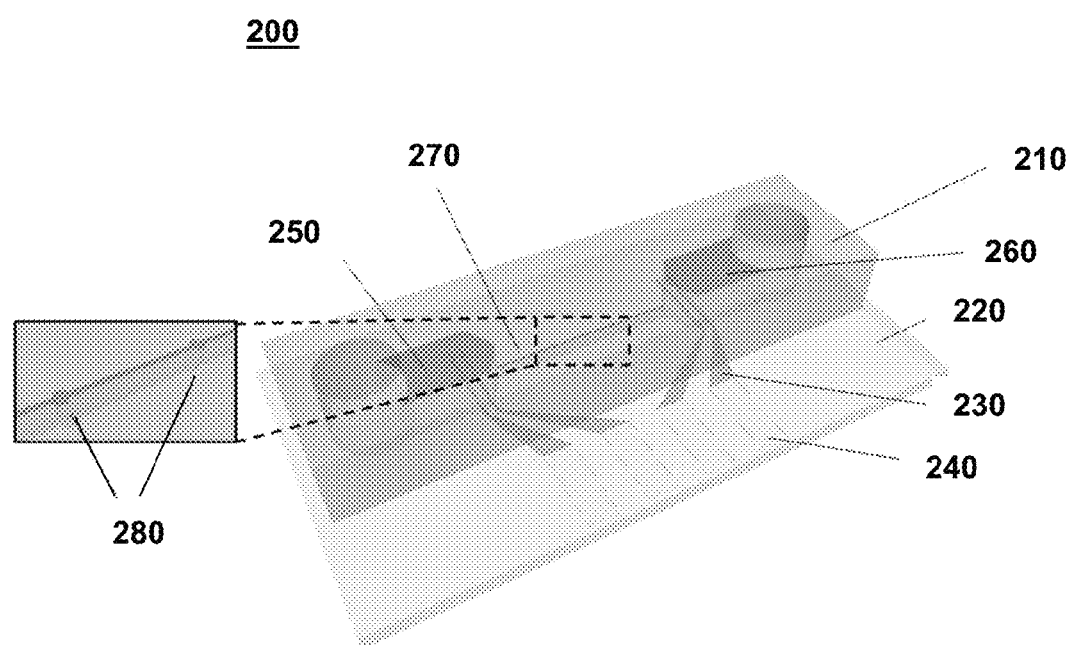
FIG. 2 shows a schematic of a device that includes a conduit with two nodes, according to embodiments of the present disclosure. A polydimethylsiloxane (PDMS) mold was bonded to a glass cover substrate, which has platinum electrodes and gold contacts (e.g., contact pads) to perform an electrical sensing measurement. The device included two reservoirs, cored with entry and exit ports, which were joined by a conduit. The conduit, which is magnified in the inset at left, was segmented into three regions, separated by the two nodes.

FIG. 2 shows a device created with soft lithography. The device 200 includes a polydimethylsiloxane (PDMS) substrate 210 that was bonded to a glass cover 220 having platinum electrodes 230 and gold contact pads 240. The substrate 210 has two reservoirs, e.g., an inlet reservoir 250 and an outlet reservoir 260, that are connected by a single fluidic channel (i.e., the conduit 270). The conduit is segmented by two nodes 280. The use of standard lithography facilitates the inclusion of as many nodes, spaced as far or close apart, as desired. A four-point (e.g., four-electrode) detector was used with a constant applied AC voltage (typically 0.2-0.4 V), to measure the current across the conduit. Subsequent data analysis, including a Fast Fourier Transform (FFT), was performed using custom-written software in LabVIEW.

Electrodes were lithographically patterned onto glass cover substrates using Microposit S1813 (Dow) resist. A 75/250/250 Å Ti/Pt/Au thin film was deposited onto the cover substrates using an electron-gun evaporator. Electrodes were gold-etched to reveal Pt electrodes and Au contact pads for measurement.

A negative-relief master made of SU-8 photoresist on polished silicon wafers was used to create the devices. Polydimethylsiloxane (PDMS) (Sylgard 184) (10:1, pre-polymer:curing agent) was poured onto the master after degassing and then cured for 1 hour at 80° C. PDMS containing the device design (including conduit with nodes) was cut from the master and entry and exit ports were cored using 16 G syringe needles. The PDMS was subsequently plasma bonded (200 mTorr, 80 W) onto the glass cover substrates containing the electrodes.

For data acquisition, a four-point (e.g., four-electrode) electrical measurement was performed using a constant applied voltage (0.32 V AC). The current measured was run through a DL Instrument 1211 preamplifier, which applied a low-pass filter at a 0.3 ms rise time. Data acquisition was done using a National Instruments PCI-6035E board with 50 kHz sampling.

Versatility of Design and Signal Measurements

To demonstrate the electronic signatures that the device produced, experiments were performed to show how the current pulse caused by a 15.45 polystyrene colloid transiting the conduit changed per the number of nodes included in the conduit. Samples used included polystyrene nanobeads (50 nm, 500 nm from Polysciences, Inc.), polystyrene microspheres (15.45 µm from Bangs Laboratories, Inc.) and latex beads (4.9 µm, 930 nm from Interfacial Dynamics Corp.). Samples were suspended in 1×phosphate buffered saline (PBS, pH 7.4) and driven through the device using a non-pulsatile pressure (~2.5 psi).

Figure 3A:
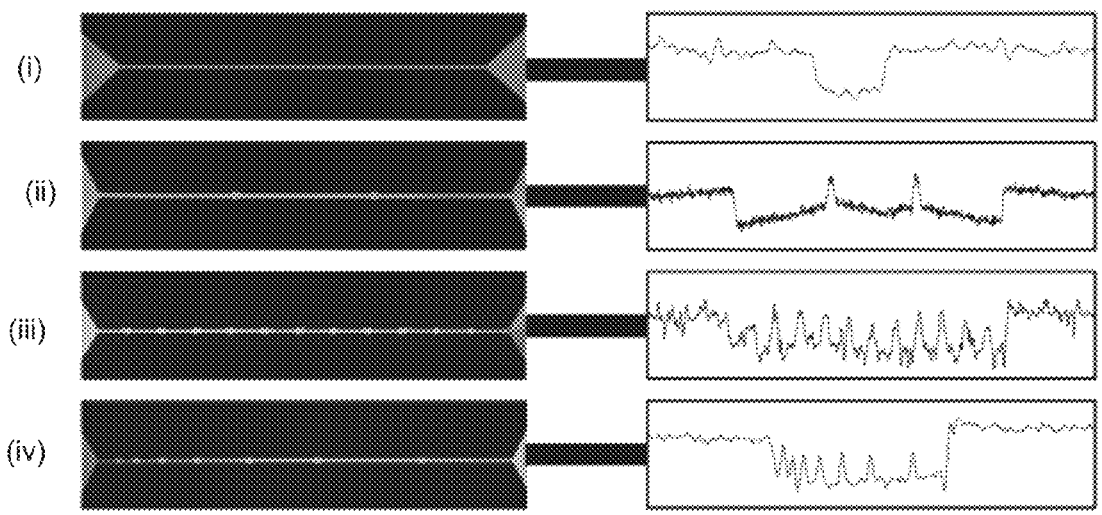
FIG. 3A shows various node-conduits and signal measurements of 15.45 µm colloids in transit, according to embodiments of the present disclosure.

FIG. 3A(panel (i), left) is a fluorescent image of a conduit that does not include any nodes. The conduit had a of size 25 µm×25 µm×800 µm (H×W×L) and the corresponding current pulse measured is shown at FIG. 3A(panel (i), right). FIG. 3A(panel (ii), left) shows a conduit that has two equally spaced nodes that are each 50 µm wide. The pulse produced FIG. 3A(panel (ii), right) was significantly different despite measuring the same-sized colloid: the current (resistance) changed as the colloid traveled through the conduit. As the colloid entered the segmented conduit, the current initially dropped from the baseline. When the colloid traveled through the first node, the current increased, and then dropped again when the colloid exited the first node. This rise and fall in current was repeated when the colloid entered and exited the next node. Finally, when the colloid exited the conduit, the current returned to the original baseline value. Such distinct current modulation was also detected when utilizing a device with twelve equally spaced nodes, as shown in FIG. 3A(panel (iii)). Changes in the current can indicate not only the number of nodes present in the conduit, but also the spacing of the nodes along the conduit, as FIG. 3A(panel (iv)) shows when a device that included eight variably spaced nodes was tested. The current pulse measured through the device reflected the node-conduit architecture: the number of nodes and their corresponding spacing in a conduit directly affected the current-pulse measurement.

Signal Modification Using Conduit Segmentation

Figure 3B:
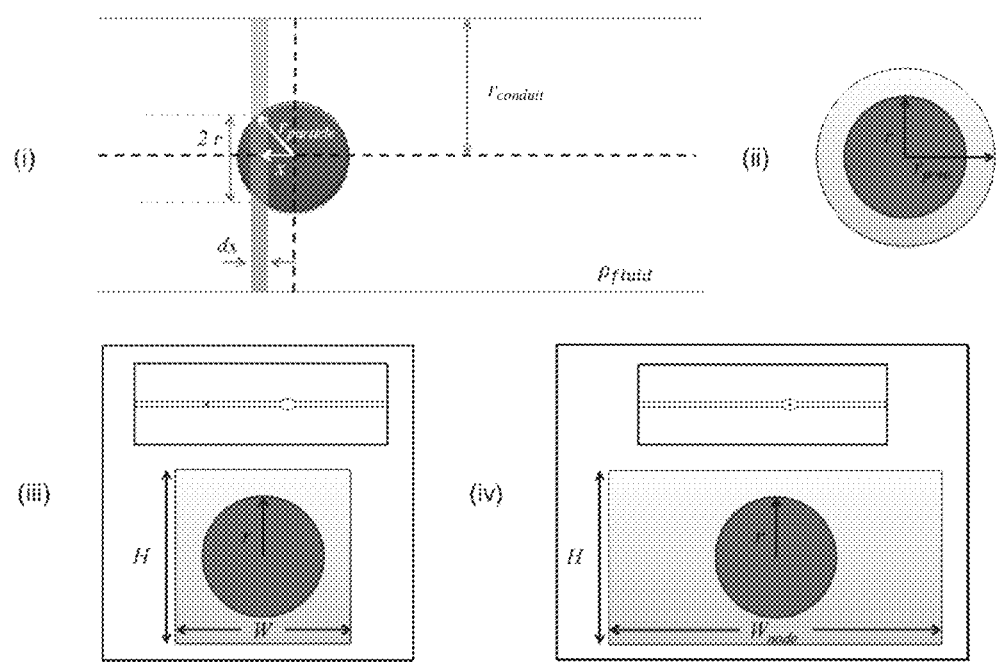
FIG. 3B(panel (ii)) shows a view of the cross-sectional slice. The darker shading represents the particle cross-section and lighter shading represents the cross-sectional area between the conduit and the particle, $\Delta A$.

The measurement that the conduit provides can be understood by analyzing the resistivity changes as a particle transits through a conduit. Assuming a non-conducting particle and a conduit with radius $r_{particle}$ and $r_{conduit}$, respectively, (FIG. 3B(panel (i))), the resistance of a cross-sectional slice of thickness dx (FIG. 3B(panel (ii))) is:

$$dR = \frac{\rho_{fluid} dx}{\Delta A} = \frac{\rho_{fluid} dx}{A_{conduit} - A_{particle}} \quad \text{Eq. 1}$$

where $\rho_{fluid}$ is the fluid resistivity and $\Delta A$ is the difference between the conduit cross-sectional area, $A_{conduit}$, and the particle cross-sectional area, $A_{particle}$. The total increase in resistance measured across the conduit due to the presence of a particle can be expressed as:

$$\Delta R = \int_{-r_{particle}}^{r_{particle}} \frac{\rho \, dx}{\Delta A(x)} - \int_{-r_{particle}}^{r_{particle}} \frac{\rho \, dx}{A_{conduit}} \quad \text{Eq. 2}$$

The above analysis assumes a cylindrical conduit. For rectangular cross-sections with width W and height H, the cross-sectional area difference of a nodal conduit slice (FIG. 3B(panel (iii))) is:

$$\Delta A_{rectangular}(x) = WH - \pi r(x)^2 \quad \text{Eq. 3}$$

where r(x) is the particle slice radius. In the nodal region of the conduit, the increased cross-sectional area difference of a conduit slice (FIG. 3B(panel (iv))) is:

$$\Delta A_{node}(x) = W_{node} H - \pi r(x)^2 \quad \text{Eq. 4}$$

where $W_{node}$ is the width of the node region. Thus, when a particle is transiting a node region with width $W_{node} > W$, $\Delta A$ is larger than that in the constant cross-section region, and in turn, the change in resistance, $\Delta R$, drops while the particle is within that node. If a conduit has a constant cross-sectional area, the change in resistance caused by the particle transiting the conduit will also be constant (Eq. 2). If the cross-sectional area of the conduit changes, then the resistance will also change as the particle transits the conduit. By utilizing the fact that a resistance measurement across the conduit at any given time is dependent on r of each cross-sectional slice of width dx at that particular time, one can specifically tailor the shape of the conduit to provide a desired resistance value, and hence, current measurement.

Detection Capabilities for Heterogeneous Populations

Because the electronic signatures produced by a segmented conduit are readily detectable, signals can be detected at lower signal-to-noise ratios (SNR) than with a conduit that does not include any nodes. Consequently, a single conduit with any given number of nodes has an improved dynamic range in detecting the size of particles. Utilizing a single microscale conduit (8 µm×10 µm×500 µm, H×W×L) that includes 4 nodes (FIG. 4(panel a)), colloids whose size spanned from 5000 nm to 50 nm were measured (FIG. 4(panel b)-(panel e)).

The detection of the smallest particle corresponded to a volume ratio $V_{particle}/V_{conduit}$ of $1.2 \times 10^{-9}$.

Fast Fourier Transform Data Processing

Figure 5:
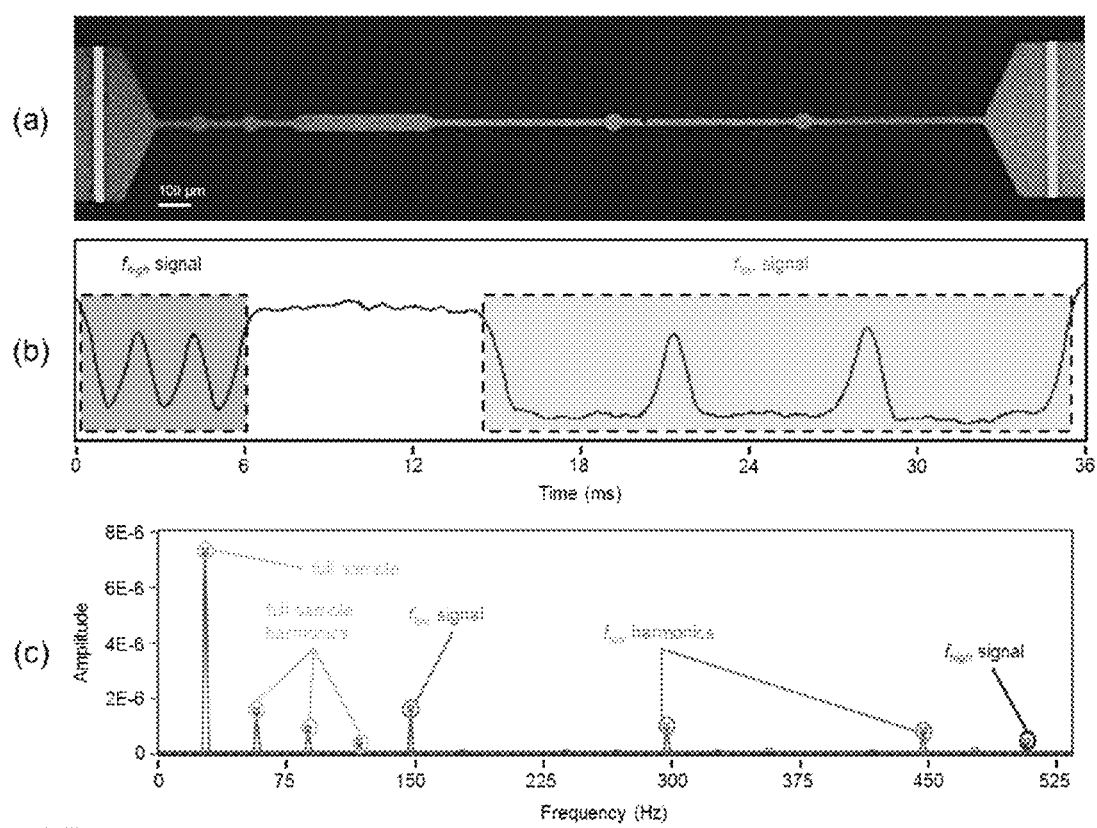
FIG. 5 shows a node-pore device with electronic signature analysis, according to embodiments of the present disclosure.

Given that the current pulse was dependent on the spatial geometry of the pore, fast Fourier transforms (FFTs) can be used to optimize the data analysis, which then allows for detection of particles transiting a conduit with nodes: the FFT power spectrum corresponds to the node spacing of a device. A microfluidic conduit (18 µm×20 µm×2400 µm, H×W×L) was made with two distinctive measurement regions, one with two 50 µm wide nodes spaced at equal 100 µm intervals along the length of the conduit and another with two 50 µm wide nodes spaced at equal 500 µm intervals along the length of the conduit (FIG. 5(panel a)). The current pulses produced when 15.45 µm colloids transited the conduit (FIG. 5(panel b)) had two distinguishable signatures within the overall signal associated with these two different measurement regions. The left highlighted region represented the high frequency portion of the signal corresponding to the part of the conduit with node spacing of 100 µm, and the right highlighted region represented the low frequency portion of the signal corresponding to the part of the conduit with node spacing of 500 µm. The associated FFT spectrum (FIG. 5(panel c)) displayed peaks corresponding to the high frequency ($f_{high}$), 100 µm node spacing segment, and the low frequency ($f_{low}$), 500 µm node spacing segment. The first peak came from the overall signal. The next three peaks represented harmonics of this first peak. The peak near 150 Hz came from the low frequency portion of the signal. The next two peaks were harmonics of this peak. The last peak came from the high frequency portion of the signal. Thus, the conduits translated spatial frequencies of the nodes into measurable temporal frequencies in the resulting signal, and current pulses that were masked by noise (low SNR) were still detected and analyzed.

Figure 6:
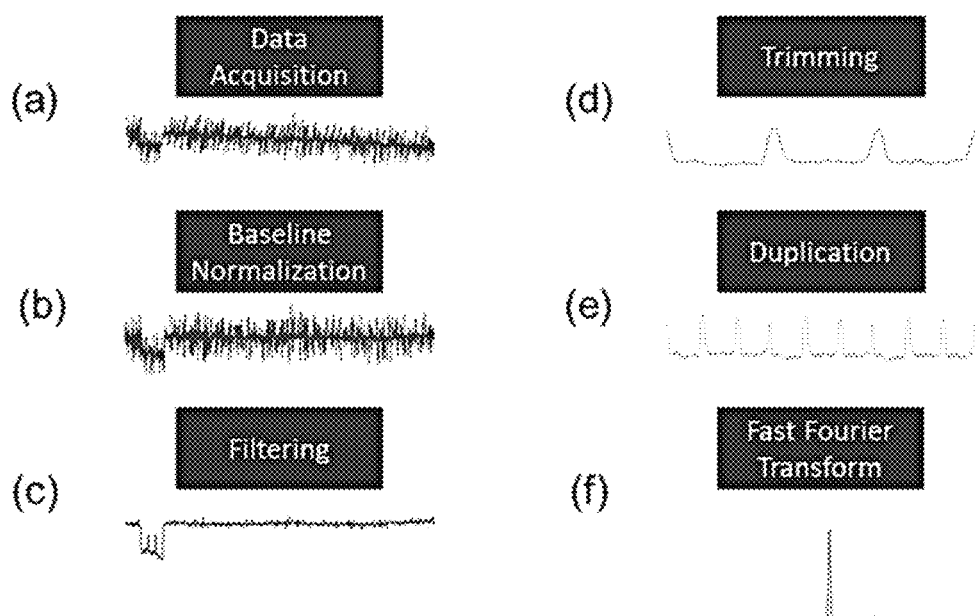
FIG. 6 shows a detection scheme for applying fast Fourier transform (FFT) analysis.

FIG. 6 shows a detection scheme for applying fast Fourier transform (FFT) analysis. FIG. 6(panel a) shows an image of raw data during data acquisition. FIG. 6(panel b) shows an image of data after normalization to a baseline fit. FIG. 6(panel c) shows data after a low pass filter was applied. FIG. 6(panel d) shows data after regions of interest were identified and trimmed using derivative cutoff detection. FIG. 6(panel e) shows duplication of the trimmed data prior to FFT analysis. FIG. 6(panel f) shows calculation of the FFT of the duplication data.

Viral Detection

Figure 4:
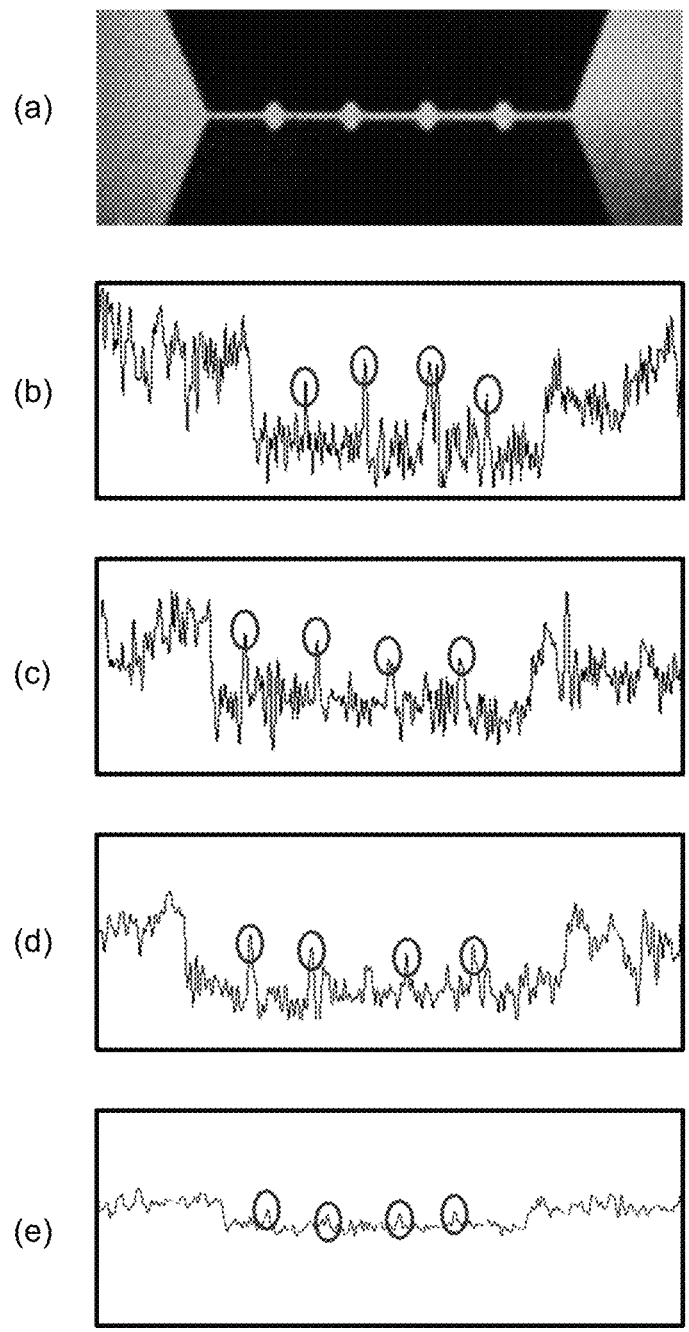
FIG. 4 shows the measurement detection capabilities of a conduit measuring 8 µm×10 µm×500 µm (H×W×L) with varying sized colloids, according to embodiments of the present disclosure.
Figure 7:
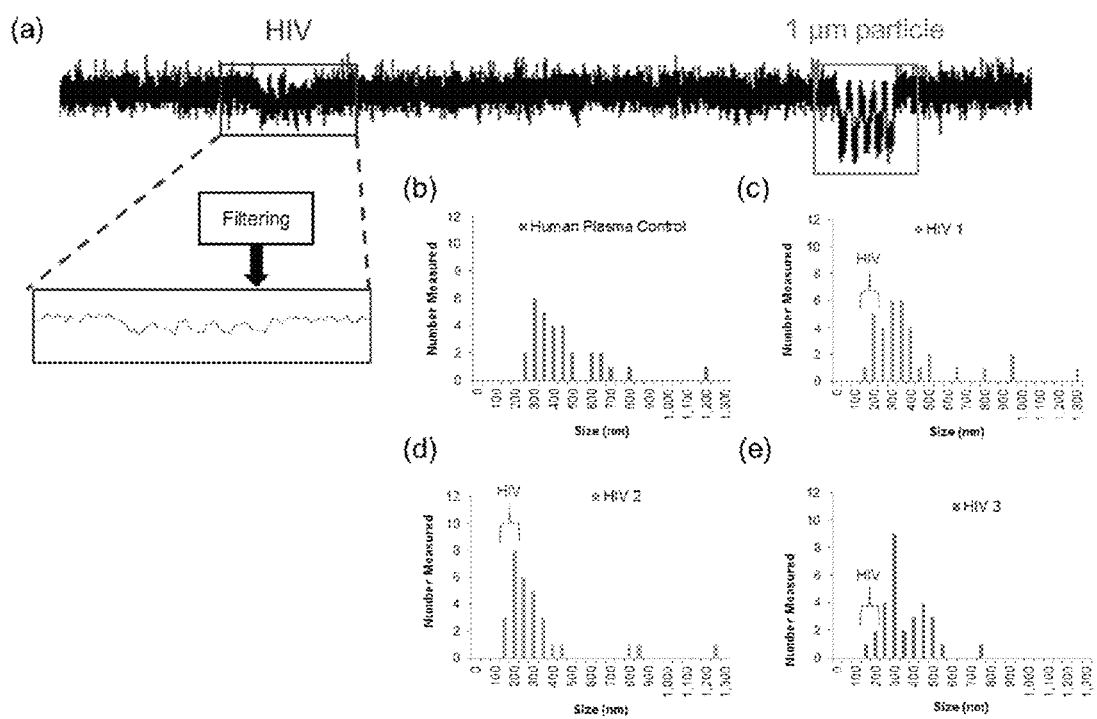
FIG. 7 shows viral detection using a conduit as shown in FIG. 4(panel a), according to embodiments of the present disclosure.

Experiments were performed to show the direct detection of HIV, whose size ranged from 100 to 150 nm in diameter depending on whether the virus was mature or immature, using the same micro-scale four-node conduit shown in FIG. 4(panel a), without antibody, antigen, or nucleic acid-based PCR testing. 50 nL human plasma containing a replication-incompetent strain of HIV (8E5) at 100,000 copies/mL was screened in three separate experiments. As a control, human plasma with no viral content was also screened. FIG. 7(panel a) shows a representative current versus time measurement. As shown, there were two distinct modulated current pulses with different magnitudes, corresponding to different sized particles. The larger pulse of the two corresponded to particles of size 1 µm in human plasma and was also found in the control. The smaller pulse corresponded to an HIV viral particle of size 100-200 nm and was not present in the control. The size distribution of particles for all the experiments was plotted (FIGS. 7(panel b)-(panel e)) and the number of viral particles detected per volume sampled corresponded to the concentration of HIV in the samples. This demonstrated the ability of microscale conduits with nodes to detect a wide range of sample sizes, even down to the nanoscale size scale of viruses.

The conduit with nodes of the present disclosure enabled the detection of nanometer sized particles with a high dynamic range and sensitivity, $V_{particle}/V_{pore}$. Amplification and filtering were not needed. Intermediate particle tracking during passage through the conduit was possible, as each node provided the location of the particle in the conduit at any given time.

Circulating Tumor Cell Detection

Figure 10:
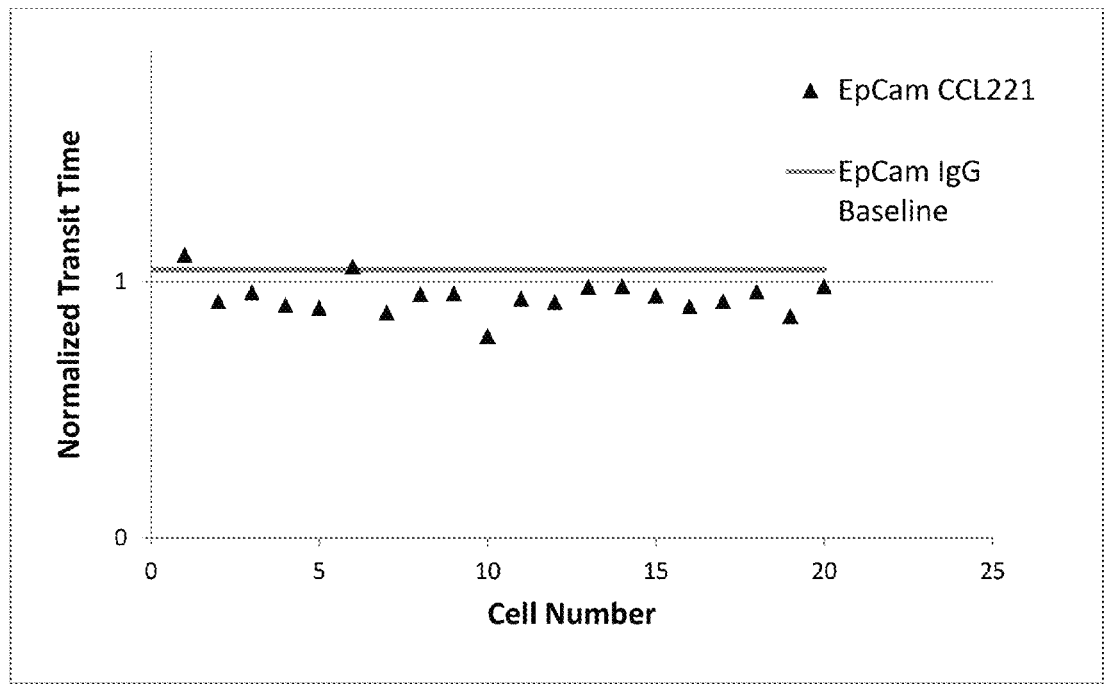
FIG. 10 shows a graph of CCL221 cells, which were EpCAM−, were analyzed with a device with an anti-EpCAM functionalized surface, according to embodiments of the present disclosure.

Experiments were performed to detect circulating tumor cells. Transit time was normalized with respect to [tau(1)+ tau(2)]/2]. The IgG baseline corresponded to another device in which the antibody region was functionalized with an IgG control. The IgG baseline was the average transit time for cells passing through the IgG control. CCL221 cells, which were EpCAM−, were analyzed with a device with an anti-EpCAM functionalized surface. Any cell *(triangle) above the IgG control was considered positive for the marker (in this case EpCAM). See FIG. 10. The experiments indicated that the screened cells were 90% EpCAM−.

Figure 11:
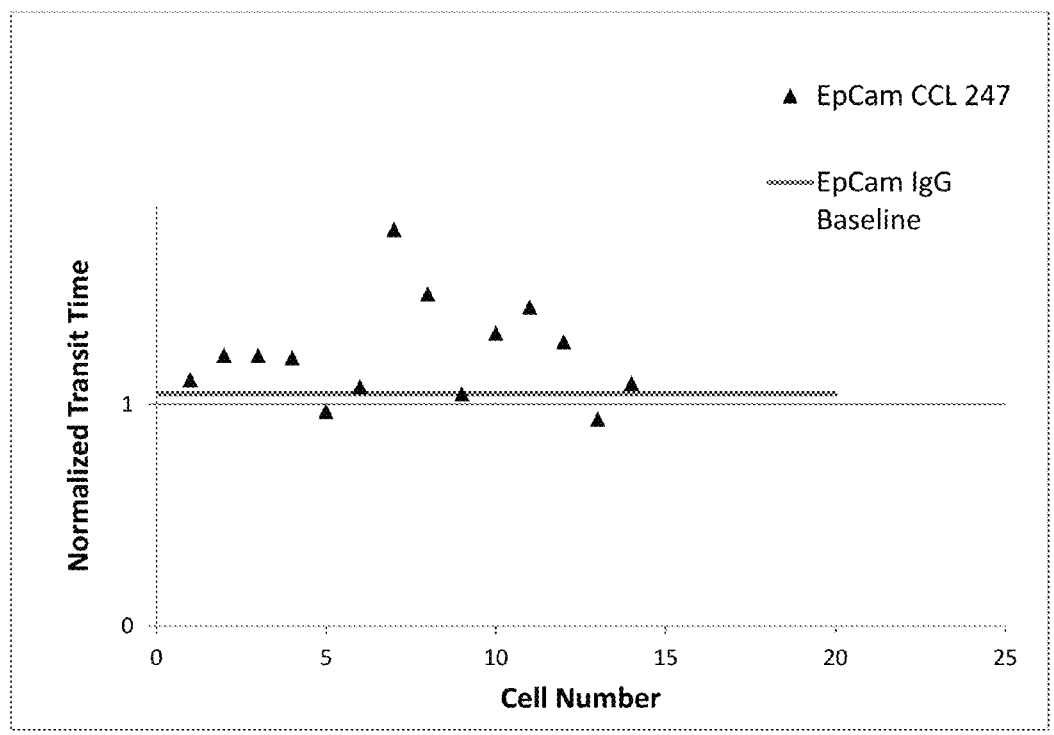
FIG. 11 shows a graph of CCL247 cells, which were EpCAM+, were analyzed with a device with an anti-EpCAM functionalized surface, according to embodiments of the present disclosure.

Experiments were performed as described above. CCL247 cells, which were EpCAM+, were analyzed with a device with an anti-EpCAM functionalized surface. Any cell *(triangle) above the IgG control was considered positive for the marker (in this case EpCAM). See FIG. 11. The experiments indicated that the screened cells were 80% EpCAM+.

Figure 12:
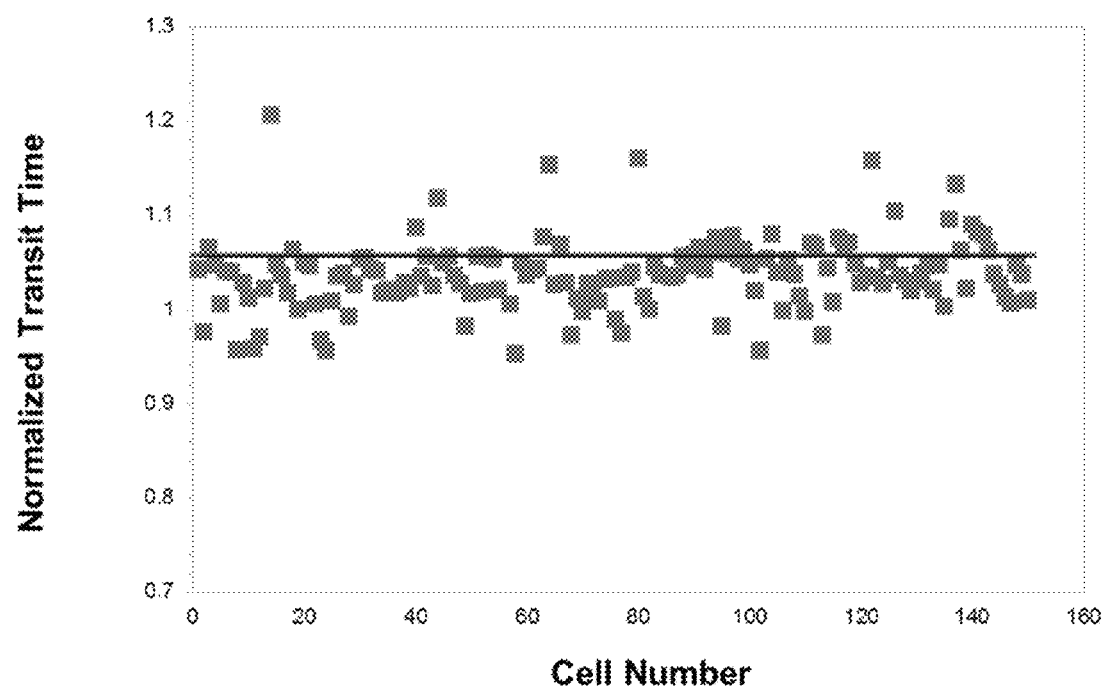
FIG. 12 shows a graph of a 1:10 mixture of HTB38: CCL220 cells which were analyzed with a device with an anti-EpCAM functionalized surface, according to embodiments of the present disclosure.

Experiments were performed as described above on mixtures of cells. A 1:10 ratio of HTB38 cells and CCL220 cells were analyzed with a device with an anti-EpCAM functionalized surface. Any cell *(square) above the IgG control was considered positive for the marker (in this case EpCAM). See FIG. 12. The experiments indicated that the screened cells were 19% EpCAM+.

Immunostaining/FACS was performed on the HTB38 and CCL220 cells, which indicated that HTB38 were 100% EpCAM+(e.g., 300/300 cells) and CCL220 were 1.2% EpCAM+(e.g., 6/494 cells), which gave for a 1:10 mixture of HTB38:CCL220 a 12.4% EpCAM+(e.g., 149/1201 cells).

Figure 13:
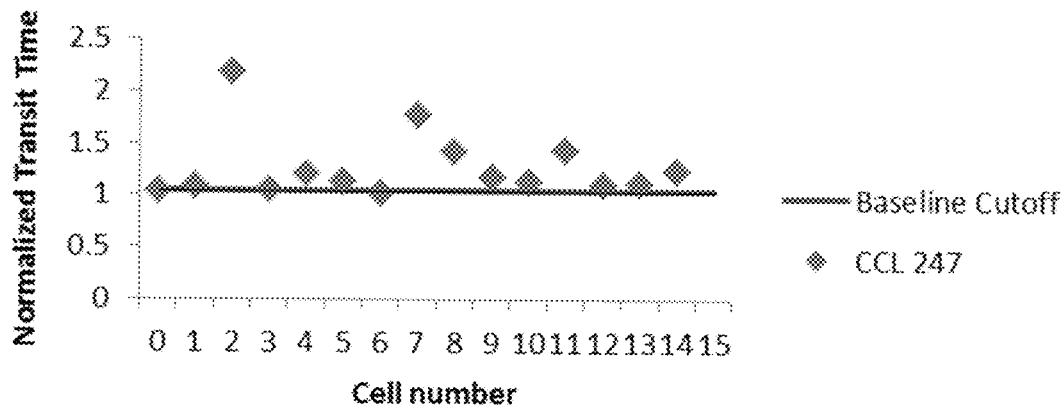
FIG. 13 shows graphs of mixed populations of EpCAM− and EpCAM+ cells which were analyzed with a device with an anti-EpCAM functionalized surface, according to embodiments of the present disclosure.
Figure 13:
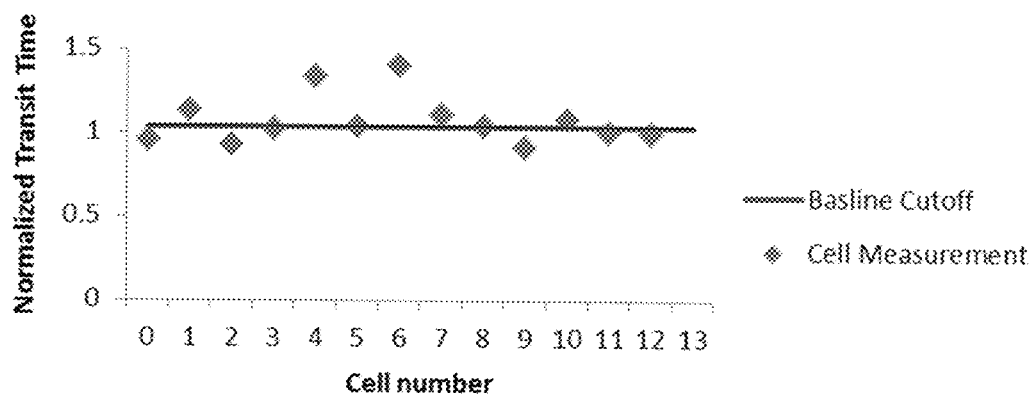

Experiments were performed as described above on mixed populations of EpCAM− and EpCAM+ cells. As shown in FIG. 13(panel a), CCL247 cells, which were EpCAM+, were analyzed with a device with an anti-EpCAM functionalized surface. Any cell *(diamond) above the IgG control was considered positive for the marker (in this case EpCAM). See FIG. 13(panel a). The experiments indicated that the screened cells were 94% EpCAM+. As shown in FIG. 13(panel b), a 1:1 mixture of CCL220 (EpCAM−) and CCL247 (EpCAM+) cell were analyzed with a device with an anti-EpCAM functionalized surface. Any cell *(diamond) above the IgG control was considered positive for the marker (in this case EpCAM). See FIG. 13(panel b). The experiments indicated that the screened cells were 46% EpCAM+. As shown in FIG. 13(panel c), a 10:1 mixture of CCL220 (EpCAM−) and CCL247 (EpCAM+) cell were analyzed with a device with an anti-EpCAM functionalized surface. Any cell *(diamond) above the IgG control was considered positive for the marker (in this case EpCAM). See FIG. 13(panel c). The experiments indicated that the screened cells were 11% EpCAM+. As shown in FIG. 13(panel d), a 100:1 mixture of CCL220 (EpCAM−) and CCL247 (EpCAM+) cell were analyzed with a device with an anti-EpCAM functionalized surface. Any cell *(diamond) above the IgG control was considered positive for the marker (in this case EpCAM). See FIG. 13(panel d). The experiments indicated that the screened cells were 2% EpCAM+.

Figure 14:
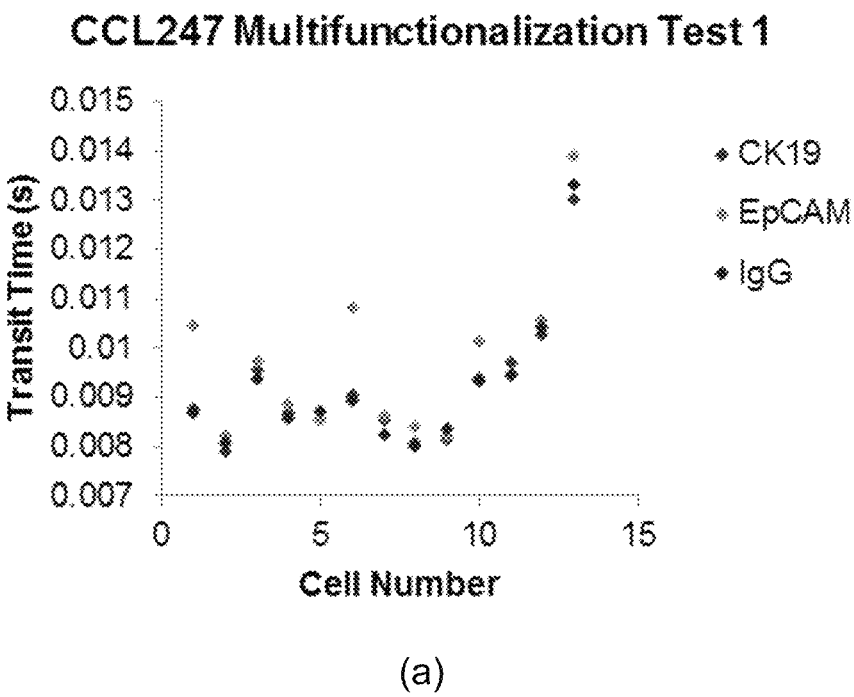
FIG. 14 shows graphs of a multiplex analysis performed with a device configured to detect three different types of cells, according to embodiments of the present disclosure.
Figure 14:
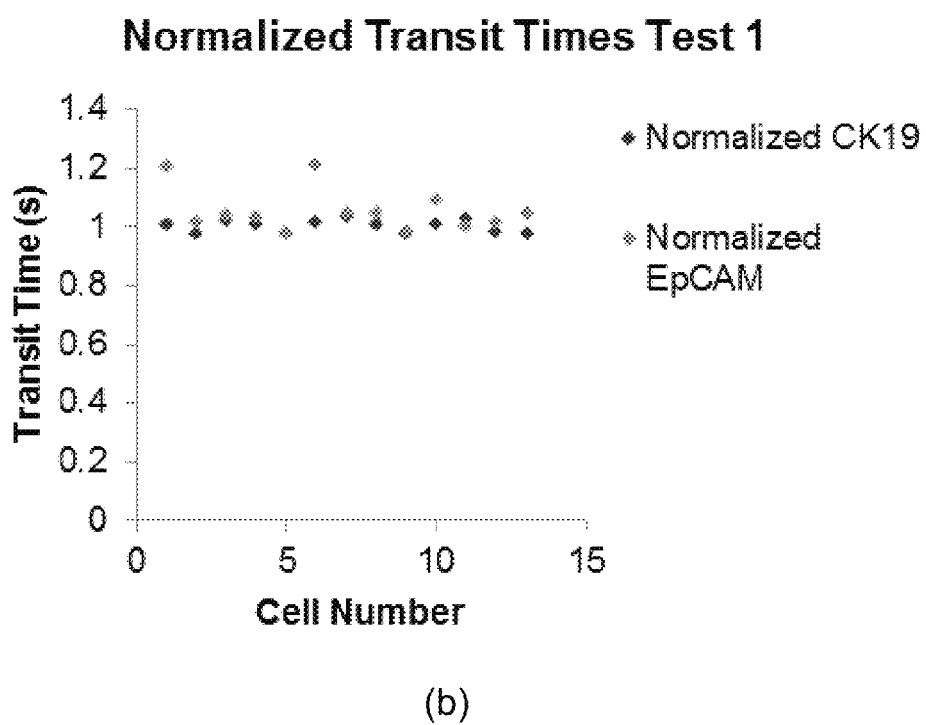

Experiments were performed using a device configured for multiplex analysis of a sample for three different biomarkers. The device included two nodes separating the conduit into three different sections, the first (upstream) section was functionalized with anti-EpCAM antibodies, the second (middle) section was functionalized with anti-CK19 antibodies, and the third (downstream) section was functionalized with anti-IgG antibodies. IgG was used as a control, as described above. CCL247 cells were screened. FIG. 14(panel a) shows a graph of transit time (seconds) v. cell number for a first screening test and FIG. 14(panel c) shows a graph of tansit time (seconds) v. cell number for a second screening test. The normalized transit times for the first and second screening tests are shown in FIGS. 14(panel b) and 14(panel d), respectively. Screening test 1 indicated that the cells were 85% EpCAM+ and 62% CK19+. Screening test 2 indicated that the cells were 86% EpCAM+ and 86% CK19+.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A device for detecting a particle in a fluid sample, the device comprising:
   a segmented microfluidic conduit configured to carry a flow of a fluid sample comprising a particle, wherein the conduit comprises an alternating pattern of regions having a smaller cross-sectional area and regions having a larger cross-sectional area; and
   a detector configured to apply a current or a voltage through the conduit and to detect a change in current or voltage as the particle passes from a region having a smaller cross-sectional area to a region having a larger cross-sectional area or from a region having a larger cross-sectional area to a region having a smaller cross-sectional area.

2. The device of claim 1, wherein the detected change in current or voltage corresponds to the presence of the particle in the conduit.

3. The device of claim 2, wherein the current is AC.

4. The device of claim 1, wherein the conduit comprises two or more regions having a smaller cross sectional area.

5. The device of claim 1, wherein the conduit comprises two or more regions having a larger cross sectional area.

6. The device of claim 1, wherein the conduit comprises a region having a smaller cross-sectional area flanked on each side by a region having a larger cross-sectional area.

7. The device of claim 1, wherein the conduit comprises a region comprising a functionalized surface.

8. The device of claim 7, wherein the functionalized surface comprises a binding member selected from a group consisting of an antibody, a protein, a sugar molecule, and an aptamer.

9. A kit comprising:
a device of claim 1; and
a buffer.

10. The device of claim 1, wherein the detector is configured to measure an amount of time for the particle to pass through the conduit.

11. A method of detecting a particle in a fluid sample, the method comprising:
passing a fluid sample comprising a particle through a segmented microfluidic conduit comprising an alternating pattern of regions having a smaller cross-sectional area and regions having a larger cross-sectional area; and
applying a current or a voltage through the conduit to produce a detectable signal that corresponds to the presence of the particle in the conduit, wherein the particle causes a detectable change in the current or the voltage as the particle passes from a region having a smaller cross-sectional area to a region having a larger cross-sectional area or from a region having a larger cross-sectional area to a region having a smaller cross-sectional area.

12. The method of claim 11, further comprising detecting the signal to determine the presence of the particle in the conduit.

13. The method of claim 11, further comprising quantifying the particle that passes through the conduit.

14. The method of claim 11, further comprising characterizing the particle as the particle passes through the conduit.

15. The method of claim 14, wherein the characterizing comprises determining whether a biomarker is present on the particle based on the signal.

16. The method of claim 11, wherein the particle is selected from the group consisting of a cell, a cellular component, a virus, a DNA, an RNA, a protein, a peptide, an antibody, a diabody, an Fab fragment, an aptamer, a polysaccharide, and a lipid.

17. The method of claim 11, wherein the particle is a polymer particle.

18. The method of claim 11, wherein the polymer particle is a polystyrene bead, a latex bead, a colloid, a magnetic particle, a dielectric particle, or a crystal.

19. The method of claim 11, further comprising measuring an amount of time for the particle to pass through the conduit.

20. A system for detecting a particle in a fluid sample, the system comprising:
a device comprising:
a segmented microfluidic conduit configured to carry a flow of a fluid sample comprising a particle, wherein the conduit comprises an alternating pattern of regions having a smaller cross-sectional area and regions having a larger cross-sectional area; and
a detector configured to apply a current or a voltage through the conduit and to detect a change in current or voltage as the particle passes from a region having a smaller cross-sectional area to a region having a larger cross-sectional area or from a region having a larger cross-sectional area to a region having a smaller cross-sectional area; and
a fluid handling system configured to provide the flow of the fluid sample through the conduit.

21. The system of claim 20, further comprising a sorter positioned downstream from the device.

* * * * *